(12) United States Patent
Daughton et al.

(10) Patent No.: US 11,430,113 B2
(45) Date of Patent: Aug. 30, 2022

(54) CANCER DETECTION SYSTEMS AND METHODS

(71) Applicant: CureMetrix, Inc., La Jolla, CA (US)

(72) Inventors: William Scott Daughton, Los Alamos, NM (US); Hoanh X. Vu, Huntington Beach, CA (US); Homayoun Karimabadi, Del Mar, CA (US)

(73) Assignee: CureMetrix, Inc, San Diego, CA (US)

( * ) Notice: Subject to any disclaimer, the term of this patent is extended or adjusted under 35 U.S.C. 154(b) by 0 days.

(21) Appl. No.: 17/008,537

(22) Filed: Aug. 31, 2020

(65) Prior Publication Data

US 2020/0402234 A1   Dec. 24, 2020

Related U.S. Application Data

(63) Continuation of application No. 15/765,470, filed as application No. PCT/US2016/054074 on Sep. 28, 2016, now Pat. No. 10,762,624.

(60) Provisional application No. 62/236,168, filed on Oct. 2, 2015.

(51) Int. Cl.
| | |
|---|---|
| *G06T 7/00* | (2017.01) |
| *A61B 5/00* | (2006.01) |
| *G06V 10/44* | (2022.01) |
| *G06V 20/69* | (2022.01) |
| *G06T 7/62* | (2017.01) |
| *G06T 7/13* | (2017.01) |
| *G06K 9/62* | (2022.01) |
| *A61B 5/055* | (2006.01) |

(52) U.S. Cl.
CPC .......... *G06T 7/0012* (2013.01); *A61B 5/7264* (2013.01); *G06K 9/6276* (2013.01); *G06T 7/13* (2017.01); *G06T 7/62* (2017.01); *G06V 10/44* (2022.01); *G06V 20/698* (2022.01); *A61B 5/055* (2013.01); *A61B 5/418* (2013.01); *G06T 2207/10081* (2013.01); *G06T 2207/10088* (2013.01); *G06T 2207/10116* (2013.01); *G06T 2207/30096* (2013.01)

(58) Field of Classification Search
None
See application file for complete search history.

(56) References Cited

U.S. PATENT DOCUMENTS

| | | | |
|---|---|---|---|
| 7,603,166 | B2 | 10/2009 | Casscells et al. |
| 2004/0109592 | A1 | 6/2004 | Bankman et al. |
| 2009/0297002 | A1 | 12/2009 | Zhang et al. |
| 2010/0166283 | A1 | 7/2010 | Grosskopf |

(Continued)

OTHER PUBLICATIONS

International Search Report and Written Opinion dated Dec. 16, 2016 for PCT/US16/54074, 8 pages.

*Primary Examiner* — Soo Jin Park
(74) *Attorney, Agent, or Firm* — Torrey Pines Law Group, PC

(57) ABSTRACT

A piece of medical information, e.g., a medical image of tissue, may be received for processing and analysis on a computing device or system. A region of the medical image may be analyzed to determine a presence of one or more contours in the region. One or more properties of the one or more contours may be extracted, where the one or more properties are inputted into a first algorithm to determine an indication of cancer for the region. The indication of cancer may be inputted into a second algorithm to generate a cancer score for the region.

20 Claims, 8 Drawing Sheets

(56) References Cited

U.S. PATENT DOCUMENTS

2010/0312072 A1    12/2010   Breskin et al.
2014/0294279 A1    10/2014   Madabhushi et al.
2016/0364862 A1*   12/2016   Reicher .................. G16H 50/50

* cited by examiner

CANCER DETECTION SYSTEMS AND METHODS

CROSS-REFERENCE TO RELATED APPLICATIONS

This application is a Continuation of U.S. application Ser. No. 15/765,470, filed on Apr. 2, 2018, which is entitled "Cancer Detection Systems and Methods," which is a National Stage Entry of PCT Application No. PCT/US2016/054074, filed on Sep. 28, 2016, which is entitled "CANCER DETECTION SYSTEMS AND METHODS", and which claims priority to U.S. Provisional Application No. 62/236,168, filed on Oct. 2, 2015, which is entitled "Cancer Detection Systems and Methods" all of which are incorporated by reference herein in their entirety for all purposes.

FIELD

The present disclosure generally relates to systems and methods for detecting and quantifying cancer cells in tissue.

BACKGROUND

Cancer is a disease that continues to kill a tremendous number of people each year and there are a significant number of health professionals that handle various aspects of cancer and its treatment. Currently, when cancer is suspected, medical information about the tissue, such as a medical image, may be gathered for the affected tissue, where a physician reviews the medical information to identify possible areas in the tissue that may have cancer cells. This analysis typically leads to an all clear diagnosis (if no areas are identified by the physician) or a recommendation for a biopsy of the tissue to confirm that any possible areas of cancer cells are in fact cancerous cells. In the context of breast cancer, the medical image is typically a mammogram. This existing approach results in an about 60% cumulative risk of a false positive and an about 20% average false negative rate. A false positive may result in a patient who did not have cancer having to endure a painful, intrusive, and unnecessary biopsy. A false negative may result in not detecting cancer as early as it could have otherwise been detected.

Other systems exist that use computer-aided detection to assist a physician in analyzing medical images. However, many of these computer-aided detection systems actually reduce the accuracy of the analysis of the medical imaging thus resulting in higher number of false positives and false negatives. There remains a need for improved cancer detection and quantification systems and methods.

SUMMARY

A computer-implemented method for cancer detection and quantification may include: receiving a medical image through a communications interface of a computing device over a data network; analyzing the medical image, with a processor of the computing device, to determine a first subset of contours in the medical image satisfying certain criteria; analyzing, with the processor, geometric attributes and contrast attributes of contours included in the first subset of contours to identify a second subset of contours based upon contours satisfying predetermined geometric and contrast attributes; selecting, with the processor, a third subset of contours from the second subset of contours that corresponds to potential calcifications, where the third subset of contours is selected based on contours within the second subset satisfying first calcification criteria; ranking, with the processor, contours included in the third subset of contours based on a selection metric, where the selection metric accounts for a combination of contrast and intensity; grouping, with the processor, the contours included in the third subset of contours into nested structures; selecting, with the processor, calcifications from the nested structures satisfying second calcification criteria; grouping, with the processor, the selected calcifications into clusters based on one or more of neighboring calcifications and a spatial cluster scale; classifying, with the processor, the clusters as benign or possible cancer by performing a regression analysis on calcifications within the clusters, edge detection, a density analysis of the clusters, and a circularity analysis of the clusters; and scoring, with the processor, the clusters using an analytic function of geometric and contrast properties of the calcifications within each cluster, and spatial arrangements of the calcifications within each cluster.

A system may include a computing device including a network interface for communications over a data network, and a cancer score engine having a processor and a memory. The cancer score engine may include a network interface for communications over the data network, where the cancer score engine is configured to receive a medical image from the computing device, and the memory is configured to store the medical image. The processor may be configured to analyze the medical image, generate a cancer score for the medical image, and transmit the cancer score to the computing device for display on a user interface thereof. Analysis of the medical image may include the steps recited above for the computer-implemented method.

In another aspect, a computer-implemented method for cancer detection and quantification includes: receiving one or more pieces of medical information for processing and analysis on a computing device, where the one or more pieces of medical information includes a medical image of tissue; analyzing, with a processor of the computing device, a region of the medical image to determine a presence of one or more contours in the region; extracting, with the processor, one or more properties of the one or more contours, the one or more properties including a geometric attribute and a contrast attribute; inputting, with the processor, the one or more properties into a first algorithm to determine an indication of cancer for the region; inputting, with the processor, the indication of cancer into a second algorithm to generate a cancer score for the region; and generating the cancer score for the region.

These and other features, aspects and advantages of the present teachings will become better understood with reference to the following description, examples, and appended claims.

BRIEF DESCRIPTION OF THE DRAWINGS

The foregoing and other objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein

DETAILED DESCRIPTION

Figure 1:
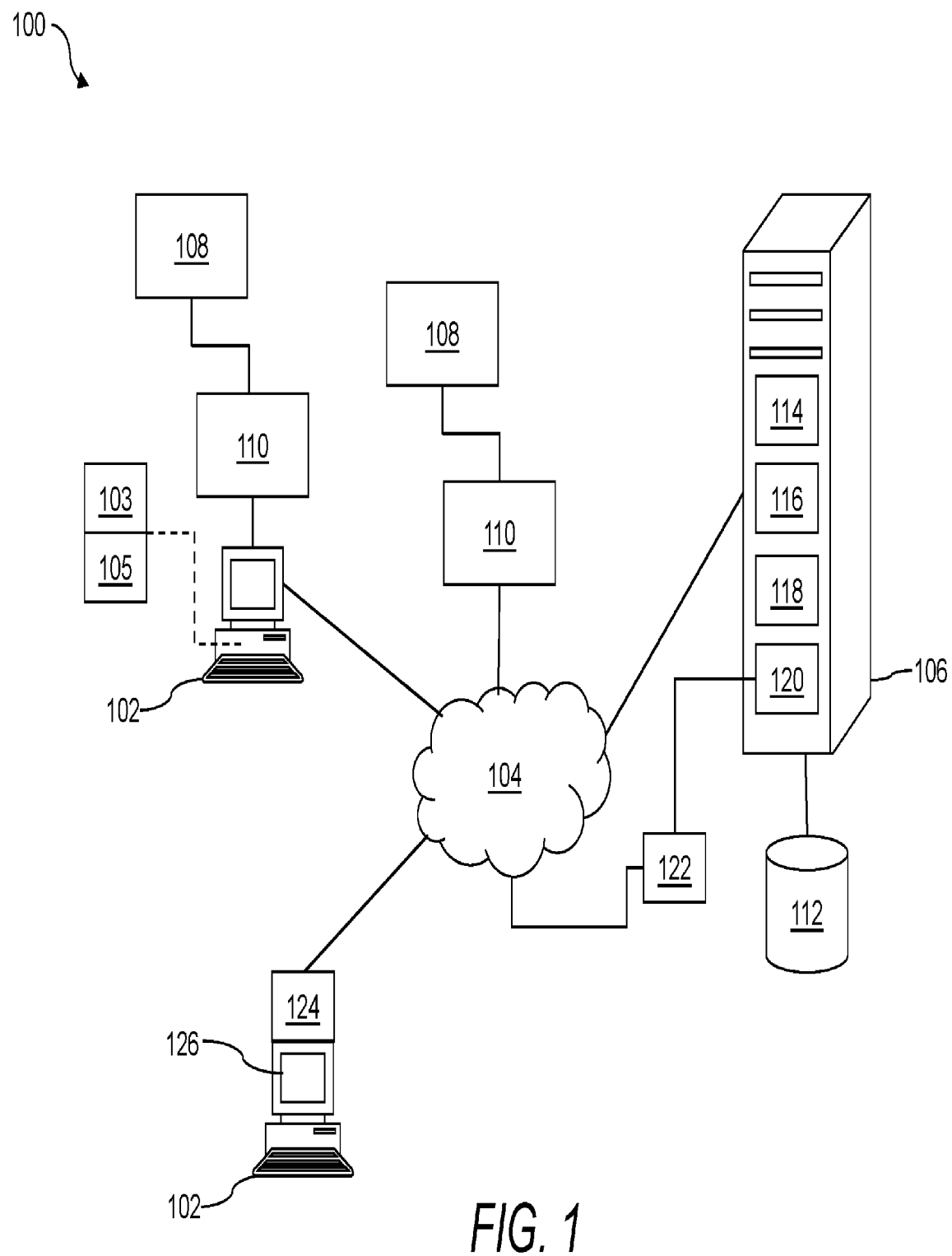
FIG. 1 illustrates a networked cancer detection and quantification system.

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately," "substantially," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," and the like, are words of convenience and are not to be construed as limiting terms.

In general, described herein are devices, systems, and methods for computer based cancer detection and quantification. As used throughout this disclosure, "detection" of cancer may include uncovering, to a particular degree or range of certainty (which may be a predetermined degree/range, or a degree/range following standard industry practice), whether cancerous cells are present (or not present) in a sample of tissue. Thus, detection may include discovering, affirming, finding, uncovering, unearthing, revealing, exposing, etc., the existence or absence of cancer cells in a sample, which can be depicted in a medical image. The cancer cells may include malignant or benign cells. As used throughout this disclosure, "quantification" of cancer may include determining, indicating, or expressing the quantity of cancer cells in a sample. The quantity of cancer cells may include a specific number, range, or threshold of cells, the size of cells or groupings of cells, and so forth. Quantification of cancer may also or instead include generating a "score" or "indication" as described herein. Quantification of cancer may also or instead include generating a "grade" or "stage" of cancer. In general, and unless explicitly stated or otherwise apparent from the context, "detection" of cancer may be included in the "quantification" of cancer and vice-versa. For instance, in an aspect, if a quantity of cancer cells is determined (i.e., a quantification), then cancer is detected. In another aspect, if a certain cancer score is determined, cancer is detected.

Although devices, systems, and methods discussed herein generally describe the detection and quantification of cancer, detection and quantification of other diseases, cells, physiological anomalies, and the like, may also or instead be enabled by the devices, systems, and methods discussed herein. Although certain embodiments discussed herein describe the detection and quantification of cancer for the specific use case of breast cancer, the devices, systems, and methods discussed herein can be adapted to detect and quantify other cancers including without limitation brain, lung, liver, prostate, bone, cervical, colon, leukemia, Hodgkin disease, kidney, lymphoma, oral, skin, stomach, testicular, thyroid, and so forth. Furthermore, although embodiments generally described herein are detecting and quantifying cancer in medical images of human tissue, the embodiments may also or instead be applicable to cancer in animals, for example.

In general, the devices, systems, and methods discussed herein may utilize medical image analysis, which may be automated through the use of various hardware and software as described herein. The medical image analysis techniques discussed herein may thus be used quantify cancer (e.g., breast cancer) and/or generate a cancer quantification. It will be appreciated, however, that the implementations discussed herein may also or instead generate a cancer quantification based on other pieces of medical information about tissue other than images as described herein and may be implemented in other ways than those described herein that are within the scope of the disclosure. In one embodiment described below, the computer based cancer quantification system and method may be used for detecting and quantifying breast cancer in humans where the medical images are mammograms.

Implementations may provide an accurate quantification of cancer that can be utilized in a number of different ways. For example, an accurate quantification of cancer may be used for an accurate detection of cancer in a piece of medical information, such as a medical image, an early detection of cancer, the growth rate of cancer, or a prediction of the likelihood of cancer. An accurate quantification of cancer may also or instead be used to reduce the number of unnecessary biopsies (i.e., reduce false positives) and reduce the number of undiagnosed cancers (i.e., reduce false negatives). An accurate quantification of cancer may also or instead be used to determine a tumor "grade," e.g., a measure of the aggression of a specific form of cancer, whether the cancer is changing or is it staying localized (in some cases one may want to leave the cancer alone rather than operate based on the tumor grade), and so forth. An accurate quantification of cancer may also or instead be used to determine how a treatment is affecting the cancer cells or is producing new cancer cells.

Moreover, the systems and methods described herein may be used to determine a type of cancer; to evaluate a physician, a shift, a clinic, a hospital, or a system-wide performance of a medical center staff; identify false positives and false negatives in a population of audited images; to train students and doctors to improve their efficacy; and to assist clinicians, doctors, care-givers, and patients to have a better understanding of anomalies found in medical images. Those of skill in the art will recognize other uses of the present methods and systems.

The devices, systems, and methods discussed herein may be used to generate a "score" that quantifies any tissue anomalies. The score may also be referred to herein as a "Q score," "Q factor," or the like. With respect to cancer, the cancer score may be expressed in any suitable or useful level of granularity such as with discrete categories (e.g., cancerous, non-cancerous, benign, malignant, cancer-free, tumor-free, and so on), or with a numerical score, alphabetic score/grade, or other quantitative indicator. For example, the cancer score may be a two-state score (e.g., cancer detected or cancer-free), a three-state score (e.g., cancer detected, cancer-free, unknown), a five-state score (e.g., unknown, cancer detected, cancer-free, benign, malignant), a range-bounded quantity (e.g., a score from 0-10, 0-100, or 0-1,000), or any other suitable score for quantifying cancer with any desired degree of granularity. The cancer score may also or instead be scaled. By way of example, tissue abnormalities may be associated with a score or the like, which may be based on a predetermined scale, e.g., 0-100, where certain known benign abnormalities would have a score close to or equal to 0 and certain known malignant abnormalities detected in advanced stages would have a score close to or equal to 100 (or vice-versa). In another aspect, cancer information may be multi-dimensional, so that multiple aspects may be independently scored. It shall be understood that the cancer score may change to indicate that cancer is more likely as the cancer cells/tumor grows and the cancer score may also change to indicate the opposite when the cancer cells/tumor shrinks. As discussed above, in one implementation, a smaller cancer score indicates a benign tumor and a larger cancer score indicates cancer.

As another example, the devices, systems, and methods discussed herein may be used to guide a radiologist analyzing a medical image, or to pre-screen, supplement, verify, or replace a radiologist's review. For example, in the context of breast cancer, a radiologist typically reviews each mammogram. It has been shown that for every 100 screening mammograms performed, 10% are recalled for subsequent procedures, and of those, only 5% are found have cancer. This indicates that the prevalence of cancer currently found by radiologists in all mammograms is only 0.5%. In other words, 99.5% of the time using current methods and techniques, there is no cancer found in the mammogram by radiologists.

Thus, the devices, systems, and methods discussed herein may be used to prescreen mammograms, score the mammograms according to a cancer score as discussed herein, and/or identify mammograms that indicate no anomalies or show only known benign anomalies (no cancer). A t the discretion of the medical image reader, those indicated areas of the image can be more efficiently analyzed for the absence of cancer. Thus, implementations may generate an indication of the absence of cancer in certain medical images and the radiologist may not need to review those medical images in as much detail based on the indication of the absence of cancer for the particular mammogram. With this pre-screening, in particular with the assistance of the automated systems contemplated herein, a radiologist may more efficiently analyze a larger number of mammograms.

As yet another example, implementations may be used to generate an assessment or prediction of the activity of a cancer for a patient (e.g., implementations can determine that, over a particular time period, a cancer will not grow significantly or has not grown significantly), which may be used to determine a treatment for the particular patient. By way of example, a patient with prostate cancer may receive an assessment that the cancer is not going to grow significantly in the next six months and the patient may then opt for a less invasive treatment plan.

In another example, a retrospective study can be conducted whereby the present systems and methods are used to analyze a radiologist's previous findings to determine whether (and at what rate) a radiologist succeeded or failed to detect cancer in a medical image, and whether a cancer score as described herein is different from the radiologist assessment. In addition, the rate of false positives and false negatives can be determined.

FIG. 1 illustrates a networked cancer detection and quantification system. As shown in the figure, the system 100 may include a client server implementation of a cancer quantification system. The system 100 may include one or more computing devices 102 that are each used by a user or an administrator to couple to and interact with, over a network 104, a backend component 106. Although a client server/web implementation of the system 100 is shown, the system 100 may also be implemented using a software as a service (SaaS) model, a standalone computer, WiFi and tablet based solutions, and other computer architectures.

The one or more computing devices 102 may include a processor based computing device that has at least one processor 103, a memory 105, persistent storage, a display, and communication circuits so that each computing device 102 can communicate with the backend component 106, display a generated cancer score, submit pieces of medical information to the backend component 106, or otherwise interact with the backend component 106 or another component of the system 100. For example, the computing device 102 may include without limitation a smartphone device, a tablet computer, a personal computer, a laptop computer, a terminal device, a cellular phone, and the like. In some embodiments, the computing device 102 may execute an application, such as a known browser application or mobile application, that facilitates the interaction of the computing device 102 with the backend component 106. The one or more computing devices 102 may also or instead include other devices, for example including client devices such as a computer or computer system, a tablet, a mobile phone, or any other mobile or fixed computing device.

The computing device 102 may include a desktop computer workstation. The computing device 102 may also or instead be any device suitable for interacting with other devices over a network 104, such as a laptop computer, a desktop computer, a personal digital assistant, a tablet, a mobile phone, a television, a set top box, a wearable computer, and the like. The computing device 102 may also or instead include a server or it may be disposed on a server, such as any servers described herein.

The computing device 102 may be used for any of the entities described herein. In certain aspects, the computing device 102 may be implemented using hardware (e.g., in a desktop computer), software (e.g., in a virtual machine or the like), or a combination of software and hardware. The computing device 102 may be a standalone device, a device integrated into another entity or device, a platform distributed across multiple entities, or a virtualized device executing in a virtualization environment.

In general, the computing device 102 may include a processor 103, a memory 105, a network interface 124, a data store, and one or more input/output interfaces. The computing device 102 may further include or be in communication with peripherals and other external input/output devices that might connect to the input/output interfaces.

The processor 103 may be any processor or other processing circuitry capable of processing instructions for execution within the computing device 102 or system 100. The processor 103 may include a single-threaded processor, a multi-threaded processor, a multi-core processor and so forth. The processor 103 may be capable of processing instructions stored in the memory 105 or the data store.

The memory 105 may store information within the computing device 102. The memory 105 may include any volatile or non-volatile memory or other computer-readable medium, including without limitation a Random Access Memory (RAM), a flash memory, a Read Only Memory (ROM), a Programmable Read-only Memory (PROM), an Erasable PROM (EPROM), registers, and so forth. The memory 105 may store program instructions, program data, executables, and other software and data useful for controlling operation of the computing device 102 and configuring the computing device 102 to perform functions for a user. The memory 105 may include a number of different stages and types of memory for different aspects of operation of the computing device 102. For example, a processor may include on-board memory and/or cache for faster access to certain data or instructions, and a separate, main memory or the like may be included to expand memory capacity as desired. All such memory types may be a part of the memory 105 as contemplated herein.

The memory 105 may, in general, include a non-volatile computer readable medium containing computer code that, when executed by the computing device 102 creates an execution environment for a computer program in question, e.g., code that constitutes processor firmware, a protocol stack, a database management system, an operating system, or a combination of the foregoing, and/or code that performs some or all of the steps set forth in the various flow charts and other algorithmic descriptions set forth herein. While a single memory 105 is depicted, it will be understood that any number of memories may be usefully incorporated into the computing device 102. For example, a first memory may provide non-volatile storage such as a disk drive for permanent or long-term storage of files and code even when the computing device 102 is powered down. A second memory such as a random access memory may provide volatile (but higher speed) memory for storing instructions and data for executing processes. A third memory may be used to improve performance by providing higher speed memory physically adjacent to the processor 103 for registers, caching, and so forth. The processor 103 and the memory 105 can be supplemented by, or incorporated in, logic circuitry.

The network 104 may include a communications path such as a wired or wireless network that uses a communications protocol and a data protocol, such as HTTP or HTTPS and HTML or JSON or REST, to allow each computing device 102 to interact with the backend component 106. The network 104 may be a wired network, a wireless computer network, a wireless digital data network, a cellular wireless digital data network, or a combination of these networks that form a pathway between each computing device 102 and the backend component 106.

The network 104 may also or instead include any data network(s) or internetwork(s) suitable for communicating data and control information among participants in the system 100. This may include public networks such as the Internet, private networks, and telecommunications networks such as the Public Switched Telephone Network or cellular networks using third generation cellular technology (e.g., 3G or IMT-2000), fourth generation cellular technology (e.g., 4G, L MT-Advanced, E-UTRA, etc.) o r WiMax-Advanced (IEEE 802.16 m)) and/or other technologies, as well as any of a variety of corporate area, metropolitan area, campus or other local area networks or enterprise networks, along with any switches, routers, hubs, gateways, and the like that might be used to carry data among participants in the system 100. The network 104 may also include a combination of data networks, and need not be limited to a strictly public or private network. The participants in the system 100 may each be configured with a network interface 124 for communications over the network.

A user 108 of the system 100 may be a patient, a doctor, a radiologist, a health care organization, an image analyst, a client, and the like. The user 108 may, using the computing device 102, submit one or more pieces of medical information 108 for quantification by the system 100 and/or receive, from the backend component 106, a cancer quantification score based on the received pieces of medical information 110. The backend component 106 may include storage 112 coupled to the backend component 106 (e.g., a memory, a database, and the like) that may store various data associated with the system 100 including a plurality of pieces of medical information 110 that may be used to generate one or more cancer quantification scores, user data associated with the system, and the like. The storage 112 may be implemented using a known software based or hardware based storage system.

The backend component 106 may be implemented using one or more computing resources including without limitation a processor 114, a memory 116, persistent memory/storage, and the like. By way of example, each computing resource may be a blade server, a server computer, an application server, a database server, a cloud computing resource and the like. When the system 100 is implemented as the client server architecture as shown in the figure, the backend component 106 may have a web server 118 or the like that manages the connections and interactions with each computing device 102, generates HTML code to send to each computing device 102, receives data from each computing device 102, and the like. The web server 118 may be implemented in hardware or software. Non-limiting examples of code include HTML, JavaScript, Python, Java, C++, and the like. Those of skill in the art will recognize other computer languages which can be useful.

The backend component 106 may include a cancer score engine 120 that analyzes pieces of medical information 110 about potentially cancerous tissue. The cancer score engine 120 may generate any indications of cancer in any regions of the image and may generate a cancer score 122 for any regions of the image in which there is an indication of cancer. The cancer score engine 120 may receive/obtain the pieces of medical information 110 about potentially cancerous tissue from a computing device 102, over a computer network from a third party, or from the storage 112 of the system 100. The cancer score 122 may be transmitted through the network 104, e.g., for display on the one or more computing devices 102. The cancer score engine 120 may be implemented in software or hardware. When the cancer score engine 120 is implemented in software, the cancer score engine 120 (and its components) m ay comprise a plurality of lines of computer code that may be stored in a memory 116 and executed by a processor 114 of the backend component 106 so that the processor 114 is configured to perform the processes of the cancer score engine 120 (and its components) as described herein. When the cancer score engine 120 is implemented in hardware, the cancer score engine 120 (and its components) may comprise a microcontroller, a programmable logic device, an application specific integrated circuit, or other hardware device in which the hardware device performs the processes of the cancer score engine 120 (and its components) as described herein. The cancer score engine 120 may include an algorithm or series of algorithms that assist in generating the cancer score 122 as discussed herein.

The one or more pieces of medical information 108 may include a medical image. The medical image may include an x-ray image, e.g., a mammogram and the like. The medical image may also or instead include magnetic resonance images (MRI), computerized tomography (CT) s can images, ultrasound images, and so on. Such images can be displayed in a number of formats including without limitation JPEG, PNG, TIFF, and the like. Those of skill in the art will recognize other image formats useful in the embodiments described herein.

The system 100 may instead be implemented as part of a standalone computer implementation of a cancer detection and quantification system. In this implementation, the cancer score engine 120 may be executed on one of the computing devices 102, e.g., by a processor 103 and memory 105, based on one or more pieces of medical information 110 stored in the computing device 102 or input into the computing device 102. The computing device 102 may have a display 126 and any other additional hardware including without limitation input/output devices such as a keyboard and a mouse as shown. The display 126 may include a user interface, e.g., a graphical user interface. The computing device 102 may also include the processor, and a persistent storage device such as flash memory or a hard disk drive and memory, such as DRAM or SRAM, that are connected to each other. When the computing device 102 is used to implement the cancer quantification system and the cancer score engine 120 is implemented in software, the memory 105 may store the cancer score engine 120 and an operating system and the processor 103 of the system may execute a plurality of lines of computer code that implement the cancer score engine 120 so that the processor 103 of the computer system is configured to perform the processes of the cancer score engine 120 as described herein.

The cancer score engine 120 may, in general, receive one or more pieces of medical information 110 about potentially cancerous tissue of a patient and, for each piece of tissue for the patient, generate one or more cancer scores 122 about one or more regions in the piece of tissue. The piece of tissue may include without limitation any piece of human tissue or any piece of animal tissue that may comprise cancer cells.

Figure 2:
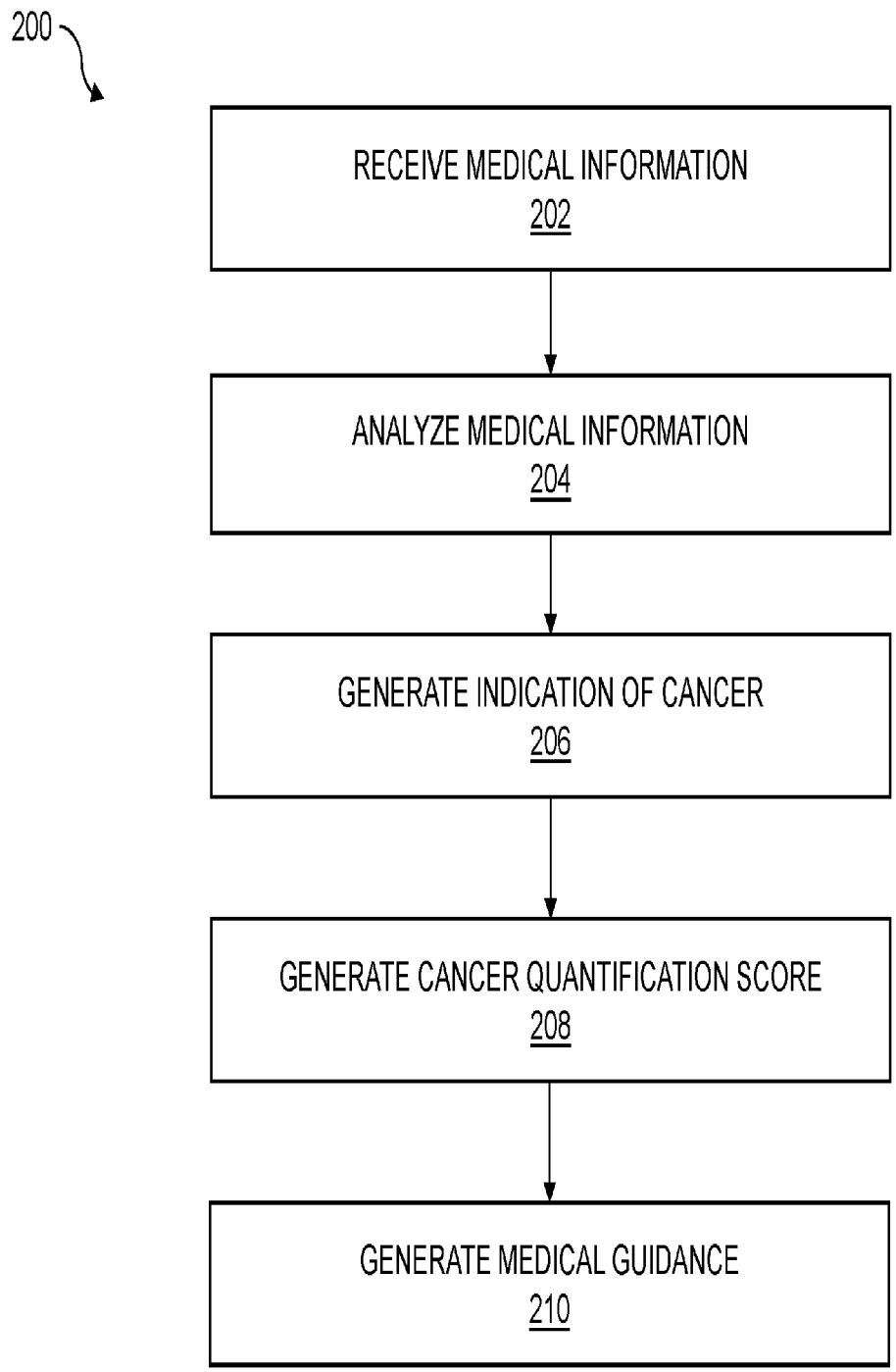
FIG. 2 is a flow chart of a method for determining a cancer score.

FIG. 2 is a flow chart of a method for determining a cancer score. The cancer score may be generated or determined by the cancer score engine. In general, the method 200 may involve processing and analyzing one or more pieces of medical information for generating, in the case of a medical image, for one or more regions of the image, an indication of cancer. For example, as described in more detail below, the method 200 may gather variables that are pertinent to cancer, programmatically analyze the piece(s) of medical information to determine values of the variables, transform these variables for use in generating a cancer indication or score, and then generate an indication of cancer based on these variables or a transformation of these variables. In the case of a medical image, a cancer score generator component may receive the indications of cancer in the one or more regions of the image and generate a cancer score for at least one region of the image. The cancer score may have a value that increases as a cancer tumor grows and decreases as a cancer tumor shrinks. In some embodiments, the cancer score may be normalized and have threshold levels so that, for example, a normalized cancer score of 1-3 indicates a benign tumor, a normalized cancer score of 4-6 indicates suspicious cells, and a normalized cancer score of 7-10 indicates that cancer is present in particular region(s) of the image.

As shown in step 202, the method 200 may include receiving one or more pieces of medical information for processing and analysis. The information may be received automatically using a networked system, delivered manually via CD-ROM, USB stick, or the like, entered manually, and the like. Those of skill in the art may recognize that there are other alternative methods of transmitting and receiving data for use in the methods and systems described herein. The medical information may include information about a patient's tissue, e.g., medical images of the tissue. The medical information may include preprocessed or raw data, which is then processed and analyzed by the systems or methods described herein. In an aspect, the cancer score engine may include a medical information analysis component that receives one or morc pieces of medical information, where the cancer score engine then processes and analyzes this information. The medical information may be automatically streamed to the cancer score engine by an uneven length preprocessed time series input. For example, the header of a DICOM file may contain information on the image contained within it including, but not limited to, the pixel resolution in physical units, criteria for interpreting the pixel intensity, and so forth.

As shown in step 204, the method 200 may include analyzing the one or more pieces of medical information about the tissue. This may include gathering variables values about the medical information (e.g., a mammogram), w here generating the indication of cancer may be based on the gathered variable values. The variables may include an intensity value for contours of any calcifications, a gradient of the calcifications, one or more characteristics about each calcification, and a hierarchical structure of the calcifications in a cluster.

As shown in step 206, the method 200 may include generating an indication of cancer. By way of example, the indication of cancer may be generated for one or more regions of the tissue in the medical images.

As shown in step 208, the method 200 may include generating a cancer quantification score. By way of example, generating a cancer quantification score may include generating a cancer score for each region of the tissue based on the indication of cancer in each region of the tissue. The cancer quantification score may indicate an absence of cancer in the region of the tissue.

As shown in step 210, the method 200 may optionally include generating guidance for a medical professional based on one or more of the indication of cancer and the cancer quantification score. The guidance may include, e.g., guidance for a radiologist based on the presence or absence of cancer in the region of the tissue. The guidance may be generated by applying rules based on the analysis of the medical information, the indication of cancer, or the cancer quantification score.

Implementations may utilize one or more algorithms for detecting and quantifying cancer from medical information supplied to the system. For example, for detecting and quantifying breast cancer, the algorithm may detect and quantify micro-calcifications in mammogram images. The algorithm may in general include (1) detecting and grouping calcifications into clusters, (2) classifying types of benign clusters, (3) quantifying clusters that are potentially malignant with a 'Q factor' as discussed herein, and (4) saving output quantities to evaluate performance. In an implementation, a first algorithm generates an indication of cancer and a second algorithm generates a cancer score.

Figure 3:
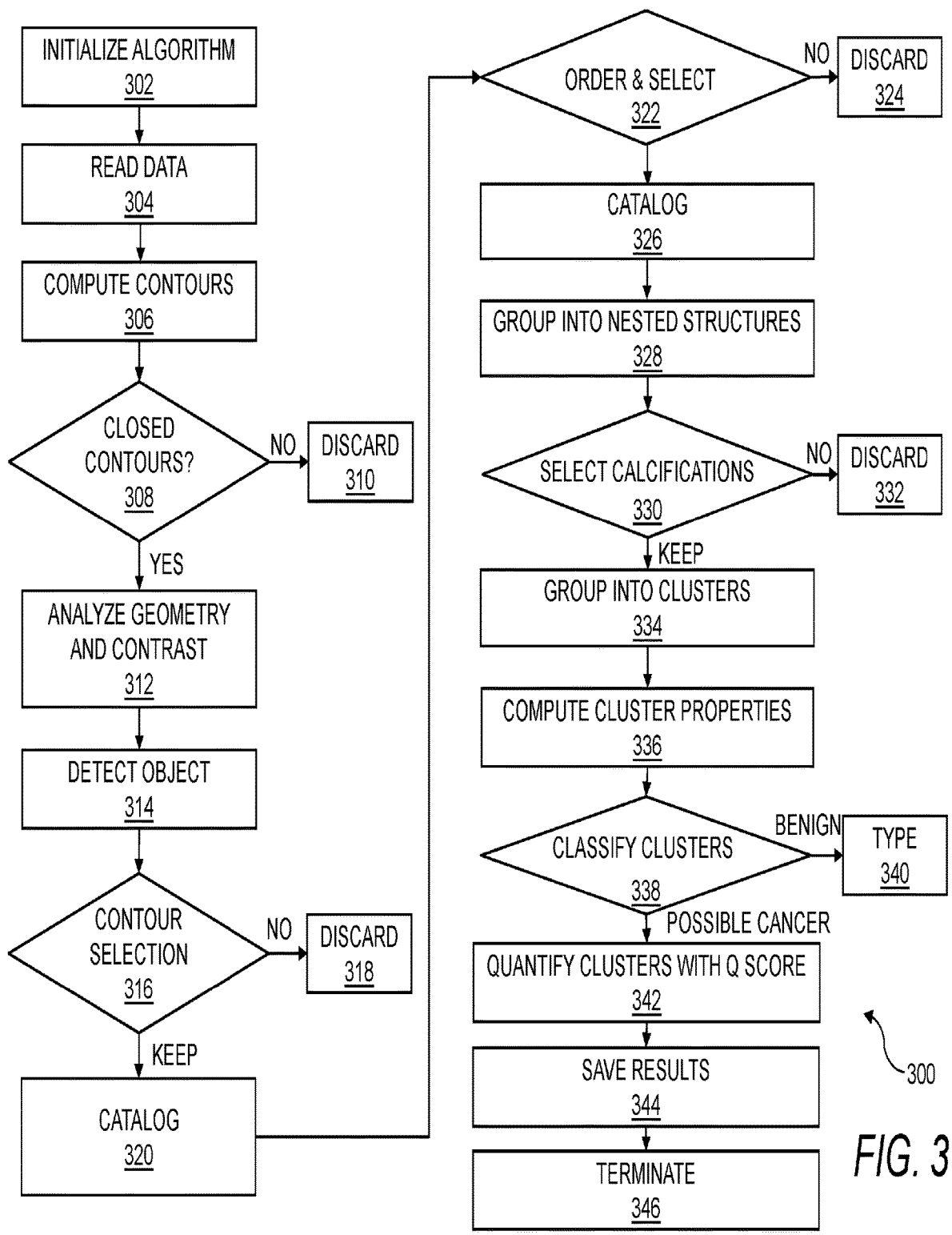
FIG. 3 is a flow chart of a method for detecting and quantifying cancer.

FIG. 3 is a flow chart of a method for detecting and quantifying cancer. The method 300 may be performed using one or more algorithms as described herein, or with assistance from an algorithm. Thus, the method 300 may be performed by a computer program product comprising non-transitory computer executable code embodied in a non-transitory computer readable medium that, when executing on one or more computing devices, performs the steps of the method 300. The method 300 may in general be performed on one or more pieces of medical information, e.g., one or more images, for detecting an object, area, region, feature, data point, piece of information, etc., of interest (e.g., a calcification, lesion, mass, tumor, and the like in a medical image).

As shown in step 302, the method 300 may include initializing an algorithm. In this step 302, memory structures may be declared and various free parameters for a model may be set. In an aspect, the parameters and model choices are spread throughout code of a computing device. In another aspect, all model parameters are set in a single place during the initialization of the algorithm, along with a clear description of each parameter including the specific section of the code/algorithm where it is utilized. This may be provided through an interactive feature for a user, e.g., a graphical user interface of a user device. In this manner, the parameters may be adjusted or inputted by a user of the method 300. In a non-interactive version, a piece of medical information may simply be received, e.g., a single image to analyze.

As shown in step 304, the method 300 may include reading data. The data may include a Digital Imaging and Communications in Medicine (DICOM) header and image data. The DICOM header may contain a range of useful information including without limitation, the side (i.e., left or right), orientation, view, protocol, date of procedure, and so forth, many of which may be listed in a filename convention. This information may be extracted for use by the algorithm—for example, in order to compare results from multiple views, or from a time series of images. Examples of DICOM tags include without limitation: (1) pixel spacing (e.g., hex tag—(0028x,0030x)), which may be useful to scale the image in terms of real physical dimensions (e.g., mm), which can compute a 'Q factor' consistently; (2) diagnostic vs screening (e.g., hex tag—(0032x, 1060x)), which may allow for inclusion or exclusion of diagnostic images from studies; and (3) patient orientation (e.g., hex tag—(0020x,0020x)), which may allow for displaying the images in a consistent manner, i.e., in the same orientation as used by radiologists in typical computer-aided design (CAD) systems, which can be advantageous when contour data is returned for display and/or analysis. For consistency in analysis, a predetermined orientation may be assigned (e.g., for mammograms—where the nipple points to the left in all images as is the industry standard). Alternatively, an orientation where burned-in lettering is displayed/oriented correctly may be utilized.

The image data may be read in with $\eta_1 \times \eta_2$ elements and converted to a 4-byte real array of intensities $I(\eta_1, \eta_2)$ for contouring as a final step for reading data.

As shown in step 306, the method 300 may include computing contours for the image. For this step 306, the intensity levels for contouring may first be selected, where an example will now be described. Typically, the side and view information are burned into an image at 100% of the maximum possible intensity, while the intensity levels within tissue in the image can be significantly less than this peak value. In order to scale the contours in a consistent manner, the maximum intensity scale may be defined as $I_{scale} = \max[I(x_1, x_2)]$ within the tissue (i.e., excluding the burned in region). By way of example, in an aspect, the following set of contours may be selected:

$$I = (0.05, 0.075, 0.10 \ldots \rightarrow 0.70) I_{scale} \rightarrow 27 \text{ levels},$$

$$(0.71, 0.72, 0.73, \ldots \rightarrow 0.99) I_{scale} \rightarrow 29 \text{ levels}, \quad \text{(Eq. 1)}$$

for a total of 56 levels. This set may provide a sufficient number of contours to work with most medical images. While contouring algorithms may return all contours within a given domain, here, an implementation may only be interested in keeping a subset of contours that include contours that are (a) closed and (b) where the contour value is larger than the surrounding area outside. This may be the first contour selection criteria identified in method 300. For example, after contouring the image, the closed loops that are found can be of two possible types:

(1) the contour value is larger than the surrounding values in the image (i.e. such contours enclose a bright spot, and potential calcifications); OR (2) the contour value is below the surrounding values in the images (i.e., such contours enclose a darker region, which may be ruled out).

The algorithm may only select the subset of contours of the first type.

As shown in step 308, the method 300 may then analyze the data to determine whether there are closed contours and/or whether the contour value is larger than the surrounding area outside. If contours do not meet these criteria, then they may be discarded as explained below.

As shown in step 310, the method 300 may include discarding contours that do not meet desired criterion, e.g., contours that are not closed.

As shown in step 312, the method 300 may include analyzing the geometry and contrast of the contours, e.g., the closed contours that were not discarded by the previous step. Contouring an image (e.g., a mammogram) with the intensity levels provided above can result in $10^5 \div 10^6$ closed contours, most of which do not correspond to clear structures of interest. To identify the contours that correspond to calcifications, masses, or external objects, the method 300 may evaluate the following geometric and contrast characteristics for each of the closed contours computed above, where each of the following are provided by way of example and not of limitation:

1. Centroid → $x_1, x_2$
2. Area → $A$
3. Perimeter → $P = \oint |d\lambda|$
4. Circle Ratio → $C_{ratio} = \left(\frac{A}{\pi}\right)^{1/2} \frac{2\pi}{P} = 0 \to 1$ for a perfect circle
5. Intensity → $I_o$ at the centroid location
6. Inward contrast → $C_{in} = I_o / I$ where $I$ is the contour value
7. Outward contrast → $C_{out} =$ $I_o / \langle I_{out} \rangle$ where $\langle I_{out} \rangle$ is the average intensity outside the contour 8. Gradient scale → $L_g^{-1} = \frac{1}{IP} \oint |d\lambda \times \nabla I| \approx \frac{1}{IP} \oint |\nabla I| d\lambda$ 9. Interior flag – ignore contours that are too close to the edge of the tissue in the image.

As shown in step 314, the method 300 may include detecting an object, e.g., detecting an object in the image. The object may be an external object, or other regions where detection may be beneficial, e.g., for exclusion in an analysis by the algorithm. For example, an image may include external objects, such as implants or diagnostic clamps. Also, some images may include regions with exceptionally poor contrast. Often there are small scale contours within the interior of these regions, which can appear as calcifications to the algorithm, and thus trigger false positives. Thus, these regions may be detected and excluded from consideration. Thus, in an aspect, the algorithm can be configured to find one or more such regions in each image, e.g., based on the following contour selection criteria:

$$A \geq 800 \text{ mm}^2 \text{ and } I \geq 0.5 I_{scale} \text{ and } C_{radio} > 0.22, \quad \text{(Eq. 2)}$$

corresponding to large bright regions with fairly smooth boundaries. For images that have objects, a number of contours may satisfy this criteria and these will typically be nested inside one another. In order to find the contour that best approximates the shape of the object, the contour that maximizes the triple product $AIC_{ratio}$ of these selection criteria may be selected. In most cases, finding the precise boundary may not be necessary, since the method 300 may just be attempting to exclude the interior area where false positives can form. In some images, false positives form just outside of the object, and thus a buffer region to exclude pixels immediately around the object may be added.

As shown in step 316, the method 300 may then select contours for discarding (step 318) or keeping (step 320).

The contours may be the contours computed above, which are then searched through for identifying potential calcifications or other features of interest. For breast cancer, the micro-calcifications of interest typically occur for a fairly narrow range of sizes (contour areas). However, depending on a particular patient, as well as the type and stage of cancer, the micro-calcifications can feature a range of contour shapes, intensity levels, and contrasts (i.e., spatial gradients). By way of example and not of limitation, the following selection can be used for most images:

1. Contours may be excluded that are within the interior of an object identified above in step 314. Also, contours may be excluded that are within a specified distance from the edge of the tissue or the edge of the image using the interior flag variable computed in step 312.

2. Contours may be included that are within the following range of areas and gradient scale:

$$0.003 \text{ mm}^2 < A < 800 \text{ mm}^2 \text{ and } L_g < 1.3 \text{ mm}, \quad \text{(Eq. 3)}$$

and that also meet one of the following criteria (a)-(e), which are provided again by way of example:

(a) Contours may be kept that enclose relatively bright regions with relatively desirable contrast values (these values may be selected by a user/administrator) and that are within a range of shapes that are not too highly deformed. This criteria may capture many of the most obvious calcifications. For example, contours may be kept that satisfy the following criteria:

$I_0 > 0.67 I_{scale}$ and $C_{ratio} > 0.65$ and $C_m > 1.06$ and $C_{out} > 1.22$ (b) Contours may be kept that have relatively weak contrast if the area is within the correct range for the smaller (weak) calcifications, and if the contours are more nearly circular or have shorter gradient scales. For example, contours may be kept that satisfy the following:

$A < 0.30 \text{ mm}^2$ and $[(C_{ratio} > 0.80 \text{ and } C_{in} > 1.04)$ or $(C_{ratio} > 0.65 \text{ and } L_g < 0.3 \text{ mm})]$ (c) Contours may be kept that are relatively large and bright. For example, contours may be kept that satisfy the following:

$(I_0 > 0.75 I_{scale}$ and $C_{ratio} > 0.69$ and $A > 1.2 \text{ mm}^2)$ or $(I_0 > 0.90 I_{scale}$ and $C_{ratio} > 0.90$ and $A > 4.0 \text{ mm}^2)$ While these may be too large to be cancerous, these types of contours may be markers of type-2 benign clusters (e.g., fatty necrosis, etc.). These benign clusters may be ignored entirely in the analysis. However, the calcifications within these benign clusters may also have a range of shapes and sizes, some of which overlap with the selection criteria in (a)-(b) above. Thus, the method 300 may find all of the members of the type-2 clusters, and group their smaller members with these larger shapes.

(d) Certain classes of contours may be kept that help reduce false-positives. For example, contours may be kept that satisfy the following:

$(I_0 > 0.62 I_{scale}$ and $C_{ratio} > 0.67$ and $C_{out} > 2$ and $A > 0.2 \text{ mm}^2)$ or $(I_0 > 0.60 I_{scale}$ and $C_{ratio} > 0.50$ and $3 \text{ mm}^2 > A > 1.5 \text{ mm}^2)$ or $(L_g < 0.4 \text{ mm}$ and $C_{ratio} > 0.67$ and $3 \text{ mm}^2 > A > 1.3 \text{ mm}^2)$ Including these types of contours may allow the method 300 to reduce some common types of false-positives when contours are grouped into nested structures, as described below. For example, some larger calcifications are hollow in the center, resulting in a ring-like structure. The choice in (a)-(b) often results in these rings being broken up into many smaller apparent calcifications. However, by including the contours that encompass the entire structure, these small nested contours may be grouped with their outer parent, and thus allow the algorithm to understand these as a single composite structure (and not multiple distinct calcifications).

(e) Contours may be kept that include relatively high central intensity, even if the contrast is relatively poor. For example, contours may be kept that satisfy the following:

$(I_0 > 0.90 I_{scale}$ and $C_{ratio} > 0.50)$

3. Full Contour Catalog. As shown in step 320, the method 300 may include cataloging the contours, e.g., cataloging the contours that are kept by the steps listed above. This may include developing a full contour catalog. This may be accomplished by saving a pointer to any contour that passes the above selection criteria. This may allow the method 300 to easily refer back to the contour at any later stage, including all of the associated geometric and contrast properties described above.

4. Order and Select. As shown in step 322, the method 300 may include determining whether to discard the contours, in which case the method proceeds to step 324, or whether to order and select the contours, in which case the method proceeds to step 326. In many images, the number of contours selected by (a)-(e) above into the full catalog is still quite large $\sim 2 \times 10^4$. The more contours that are kept can increase the overall sensitivity, but can also lead to much longer analysis times in following steps of the method 300. Furthermore, keeping too many contours at this phase may lead to more false-positives. For these reasons, another selection process may be used that restricts the total number of contours that are considered to a predetermined number, e.g., $N_{max}=6000$. In any given image, the method 300 is typically looking for the contours with the best overall combination of intensity and contrast, since these are the ones that are most apparent to a human eye. However, the absolute value of the intensity and contrasts might be different in various images, even for the same patient. Thus, the contours in the primary library may be rank ordered based on the following:

Selection Metric=$4(C_{out}-1)+I/I_0$,

In this manner, the contours with the relative best combination of contrast and intensity may be found at the top of list. In essence, in an aspect, the method 300 is scoring the contours on a relative scale for each image.

5. Primary Contour Catalog. As shown in step 326, the method 300 may include cataloging the contours, e.g., into a primary contour catalog or the like. This may be accomplished through saving a list of pointers to the first $N_{max}=6000$ contours identified by the above ordering (or whatever number is selected). This allows the method 300 to easily refer back to the best contours, including all of the associated geometric and contrast properties described above.

Figure 4:
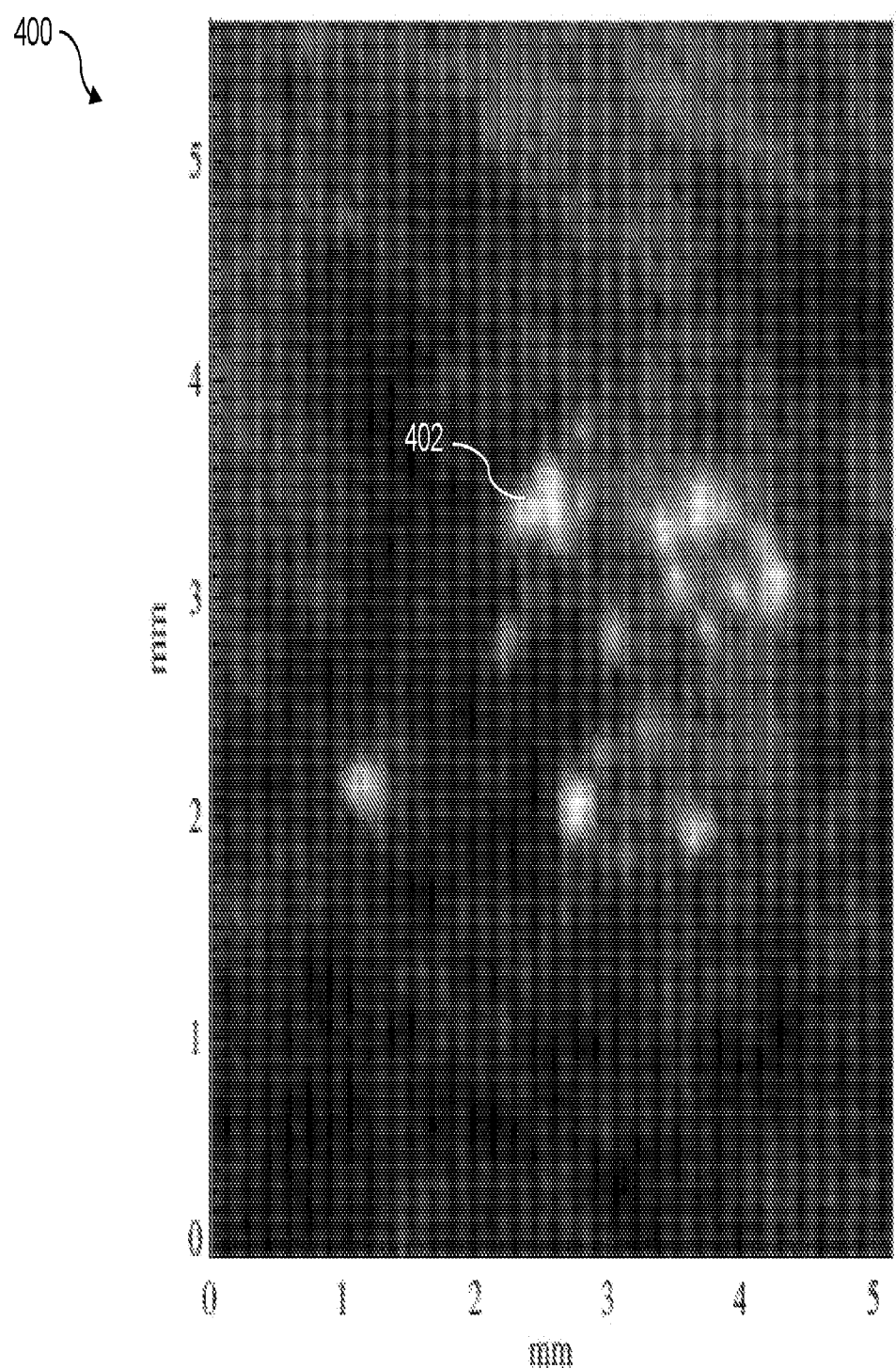
FIG. 4 depicts a medical image of calcifications in a patient's tissue.
Figure 5:
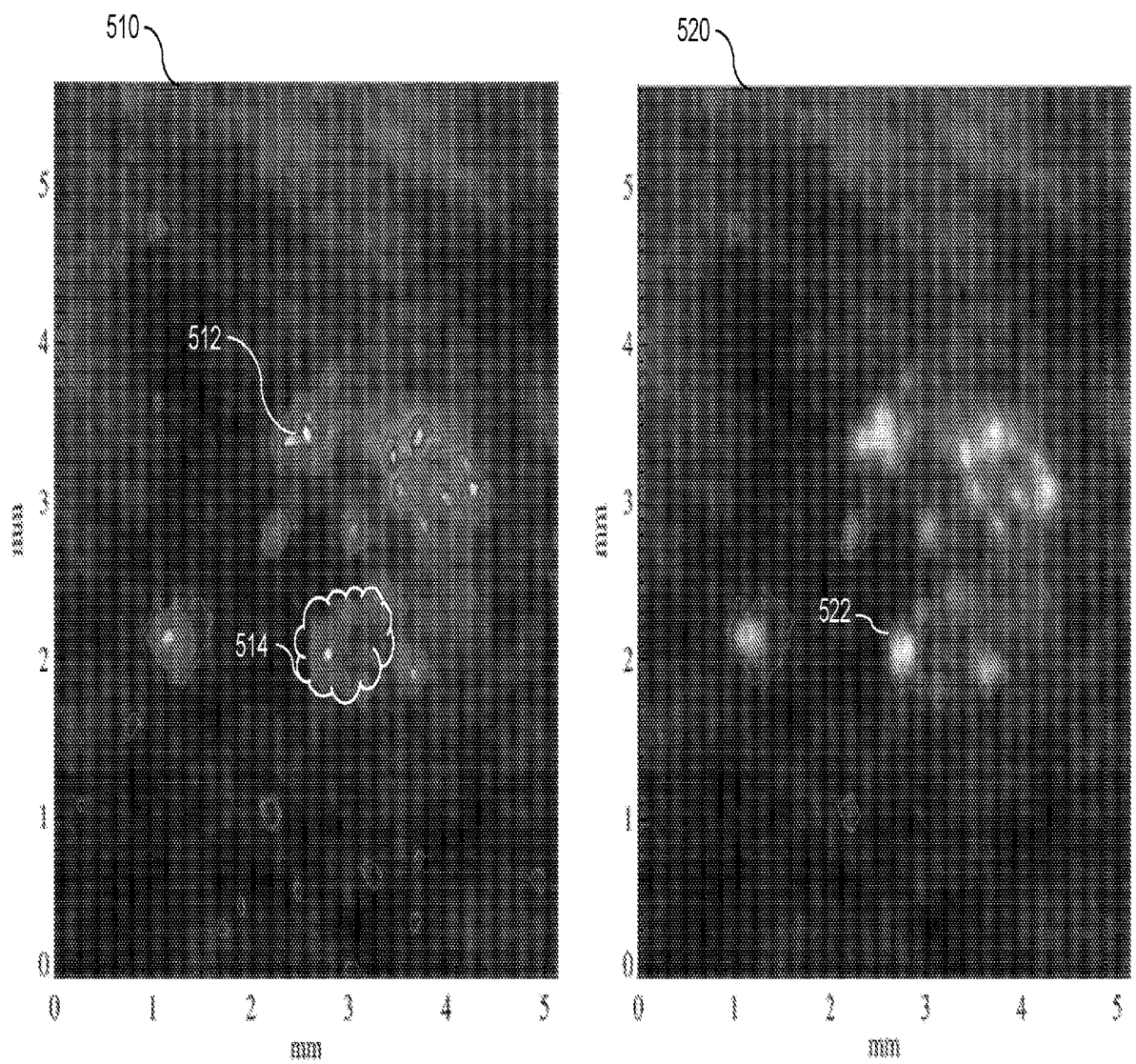
FIG. 5 illustrates an example of a selection process for a malignant cluster of micro-calcifications.

As shown in step 328, the method 300 may include grouping the contours into nested structures/hierarchies. After completing the selection processes described above, there may only be $N_{max}=6000$ contours stored within the primary catalog (or whatever number is selected above). However, in most images, only a small fraction of these contours will correspond to true calcifications. Furthermore, as illustrated in FIGS. 4 and 5 described below, there may be at least several nested contours associated with each, and up to ten or more nested contours for calcifications with a strong intensity contrast. For any given calcification, it is desirous to identify a contour that characterizes the shape of the structure. To accomplish this, the primary library may be sorted through and the contours may be grouped into nested hierarchical structures. The outer most contour (parent) in each nested series may correspond to the shape, while the inner nested contours (children) can be used to precisely measure variations in contrast across the structure, as described below when selecting calcifications from the nested contours.

For example, the $N_{max}$ contours may be first sorted according to the area enclosed by each. Next, starting with the largest contour (call top level the "parent"), the contour library may be searched to find the next smallest contour in the list that exists inside the area enclosed by the top level (parent). This would be the first "child," which may be grouped as part of this nested structure, and excludes from subsequent searches below. Next, the library may be searched again to find the next largest contour that is inside the top level parent (this one will have a smaller area than the first child). Normally, in simply nested structures, this contour would also be inside the first child, but that is not always the case. One could have multiple "peaks" inside the overall parent contour, and this can be useful for looking at the internal structure of masses. The library may be searched until no more contours that are inside the top level parent. Then, the next largest contour in the library, which has not yet been grouped, may be searched to repeat this process.

After completing this step, there may be a list of the outer contours for each nested series, and a list of pointers to the inner nested contours for each of these structures. Some fraction of these nested structures may correspond to calcifications, but others may not. In order to aid in a final selection, the following properties for each nested series may be computed, which are provided by way of example and not of limitation:

1. Contour Derivatives—To identify calcifications, it may be desirous to precisely characterize how rapidly the intensity varies across the structure. Already, the method 300 may have computed several quantities that characterize this same general idea in an average sense (i.e., the inner $C_{in}$ and outer $C_{out}$ contrast described above) and for a local gradient scale—$L_g$. Once the contours are grouped into nested structures, the method 300 may compute the fractional change in area and/or intensity between any two nested contours in the structure. After trying a range of possibilities, the following two parameters may be defined:

$$\delta A = \left(\frac{A_i - A_{i+1}}{A_i}\right)_{min}, \quad \delta I = \frac{\max(I_i)}{I_1} \qquad \text{(Eq. 4)}$$

where the nested contours may be indexed from $i=1 \rightarrow \mathcal{N}$, with $i=1$ corresponding to the outer contour and $\mathcal{N}$ the innermost. Here, $\delta A$ may be the minimum fractional area change between any two nested contours in the structure, and $\delta I$ corresponds to maximum fractional intensity change between the inner nested contours and the outermost contour that defines the shape. Small values of $\delta A \ll 1$ may correspond to tightly nested contours, where the local gradient in intensity is large, while values of $\delta I > 1$ measures the fractional intensity variation across the set of nested contours (very similar to the inner contrast $C_{in}$ discussed above).

2. Grouping Parameter. As will be discussed below with reference to grouping the contours into nested structures, one can accurately identify most of the clear calcifications using simple thresholds on $\delta A$ and $\delta I$. However, a reasonable threshold on these parameters may often miss weaker calcifications and/or in some cases entire clusters if the calcifications are less distinct. Furthermore, if one lowers the thresholds to capture these missing clusters, it may result in an unacceptable increase in false-positives in other images. The basic problem may include the following: if these weaker calcifications are judged purely by themselves, it may often be unclear (even to the human eye) whether they are truly a calcification or not. However, these weaker structures are often far more interesting if they are grouped together, with the right size and right spatial separation. To put this idea into practice, a new collective parameter that characterizes these groupings may be used. To proceed, each of the nested structures identified in as a potential calcification may be viewed and the following parameter for the ith structure may be evaluated:

$$dQ_i = \sum_{j \neq i}^{M} q_i q_j F(r_{min}, r_{max}, r_{ij}) \qquad (Eq. 5)$$

where the summation is over the M other nested structures in the image, $r_{ij}$ is the separation distance, and $q_i$, $q_j$ are statistical weights defined by:

$$q_i = (I_{oi}/I_{scale}) \min[\mathcal{N}_i, \mathcal{N}_{max}] F(a_{min}, a_{max}, A_i) \qquad (Eq. 6)$$

where $I_{oi}$ is the central intensity, $A_i$ is the area of the ith calcification, $\mathcal{N}_i$ is the number of nested contours, and $\mathcal{N}_{max}$ is a limit placed on the importance of nesting in the weight. Finally, the following selection function may be defined:

$$F(c_{max}, c_{min}, x) = C_{norm} \exp[-(x/c_{max})^2](1 - \exp[-(x/c_{min})_2]) \qquad (Eq. 7)$$

where $C_{norm} = (1+\xi)^{((1+\xi)/\xi)}/\xi^\xi$ is a normalization constant ($\xi \equiv (c_{min}/c_{max})^2$), and $c_{min}$, $c_{max}$ are constants that set the minimum and maximum scales of interest for any given quantity. For example, in Eq. 5 the selection function is applied to spatial separation, and the constants ($r_{min}$, $r_{max}$) are used to select a relevant range of separations. The function F may be constructed to reach a maximum value of unity between this range of scales, and then to fall off exponentially for separations outside this specified range. Likewise, when applied to Eq. 6, the selection function may maximize within the specified range of areas ($a_{min}$, $a_{max}$) and fall off rapidly outside this range. Thus, $dQ_i$ may have desired properties. In the absence of neighbors (i.e., within a few $r_{max}$), the value of $dQ_i$ may remain small. However, the value of $dQ_i$ may increase quadratically with the number of neighbors, if they are within the right range of separations, and have the right range of sizes to be of concern. Furthermore, the value may increase with the central intensity of the potential calcifications, and with the number of nested contours within each, both of which may correlate with visibility to the human eye.

As shown in step 330, the method 300 may include selecting calcifications from the nested contours, where, if the calcifications are not selected the method 300 discards the calcifications as shown by step 332, and where, if the calcifications are selected, the method 300 proceeds to step 334.

At this point in the method 300, all contours may have been found and characterized, contours may have been eliminated that occur inside objects, the most interesting contours may have been selected, and the contours may have been grouped into nested structures, with the outermost contour representing the shape and the inner contours providing additional information on the internal gradients. The final selection for calcifications may be made based on the following two criteria, which are provided by way of example and not of limitation:

1. Strong Calcifications→δA/δI<0.15

This threshold on the contour derivate (see Eq. 4) may capture most of the clear calcifications with sharp boundaries. This selection may be made regardless of whether the calcification has any close neighbors.

2. Weaker Grouped Calcifications→δQ$_i$<3

This threshold on the grouping parameter (see Eq. 5) may select weaker calcifications that are grouped together appropriately (as discussed above). Note that the threshold value of δQ$_i$ may be dependent on the scaling parameters chosen in Eqs. 5-7. Ultimately, it may be desirable for these choices to be consistent with the scaling parameters chosen below, which are used to compute a 'Q score' for each cluster.

As shown in step 334, the method 300 may include grouping calcifications into clusters. After identifying all calcifications within the image, next, they may be grouped into clusters according to the following procedure. A spatial cluster scale (e.g., $R_c$=7 mm) may be defined, and for each calcification the number of neighbors within this range is counted. In addition, a minimum number of calcifications to consider as a cluster (e.g., $N_{min}$=3) may be specified. Next, the method 300 may start with the calcification with the largest number of neighbors, which is used to form the first cluster. New calcifications may be recursively added to this cluster, until there are no remaining calcifications within a distance $R_c$ of any member. After finding all members of first cluster, the method 300 may proceed to the next unassigned calcification and repeat this process until all calcifications that should be grouped into a cluster have been assigned. In an aspect, only calcifications with at least two neighbors (i.e., three members) are grouped into clusters. Calcifications that are not assigned to a cluster may be ignored completely for the rest of the method 300.

This approach for forming clusters may be advantageous, and may depend only on the scale $R_c$. In most images, the actual clusters in the tissue (e.g., breast) are well separated, and this approach works well. However, in images with many vascular clusters and/or other types of benign calcifications, it may become difficult to separate out new (potentially cancerous) clusters from the pre-existing background of benign clusters. Indeed, the cancer may appear next to a vascular cluster. In this case, the clustering approach may group the new cancer together with the vascular, which may result in misclassification, where prevention/accounting for this is discussed below.

As shown in step 336, the method 300 may include computing cluster properties. To aid in the classification process, it may be useful to characterize the distribution of calcifications within the cluster. If the centroid is identified for a calcification by the ordered pair ($x_1$, $x_2$), then the cluster centroid can be defined as:

$$\bar{x}_i = \frac{1}{W} \sum_{n=1}^{N_c} w_n x_i \qquad (Eq. 8)$$

$$W \equiv \frac{1}{W} \sum_{n=1}^{N_c} w_n,$$

where $w_n$ is the weight for the nth calcification and $N_c$ is the number of calcifications within the cluster. In an aspect, the outward contrast of each calcification for the weights $w_n = C_{out}$ is used. Next, a displacement matrix for each cluster may be defined:

$$D_{ij} = \frac{1}{W} \sum_{n=1}^{N_c} w_n (x_i - \bar{x}_i)(x_j - \bar{x}_j), \qquad (Eq. 9)$$

where again the contrasts for the weights may be employed. This symmetric positive-definite matrix may have two real eigenvalues ($e_1$, $e_2$) and two eigenvectors ($d_1$, $d_2$), which can be used to define the following quantities, which are provided by way of example and not of limitation:

1. Cluster Half-Length → $L - \sqrt{e_1}$, where $e_1$ is the maximum eigenvlaue of $D_{ij}$ 2. Cluster Half-Width → $w = \sqrt{e_2}$, where $e_2$ is the maximum eignevalue of $D_{ij}$ 3. Aspect Ratio → $A = w/L$ 4. Principal Axis →

$d_1$ vector aligned with long direction in the cluster

5. Packing Fraction → $P_f =$ $$\frac{\sum_i A_i}{4Lw} - \text{(area inside calcifications)/(approximate cluster area)}$$

For each cluster, the method 300 may also compute the mean and standard deviation of the geometric and contrast properties described above, including, e.g., intensity, contrast, area, and so forth.

As shown in step 338, the method 300 may include classifying clusters as benign, in which the method 300 proceeds to step 340, or classifying clusters as possible cancer or cancerous in which the method proceeds to step 342.

Calcifications may form within tissue over a wide range of scales and for a variety of reasons. Calcifications may be of benign origin, or clusters of micro-calcifications may be indicative of cancer. Typically, benign calcifications are more common. Thus, when used as a screening tool, the large majority of clusters identified by the method 300 are expected to be of benign origin. The strategy of the method 300 may thus be to identify and exclude the most common types of benign clusters, and then to score the remaining clusters with the 'Q factor' as described below.

If the clusters are classified as benign, the method 300 may classify a type for each the cluster/calcification, which is illustrated by step 340. Some types of benign clusters are provided below by way of example and not of limitation.

Type-1: Vascular

A common type of benign cluster is associated with vascular calcifications. While these are of potential interest in studies of cardiovascular disease, these clusters may not be relevant to cancer (e.g., breast cancer). However, if vascular calcifications are present within a given image, the method 300 may identify a large number of calcifications organized along the vessel wall. Unfortunately, the range of spatial scales and separation distances for these vascular calcifications often overlaps with the micro-calcifications relevant to cancer (e.g., breast cancer). Thus, one often cannot differentiate based on the Q factor discussed below. Instead, other approaches to exclude these from consideration may be utilized.

Vascular calcifications are usually easy to spot visually, since they are well-organized along the wall of the tubular vessel. As such, at least two strategies may be used to automatically identify these vascular calcifications, i.e., using an algorithm or the like. First, the high-degree of spatial correlation can be measured, e.g., by performing a regression analysis on the positions of the calcifications. An alternative and potentially complementary approach is to employ edge detection techniques to identify the vessel walls, and then to exclude calcifications that are located along these structures.

In an aspect, the approach is based on performing a regression analysis to a polynomial of specified order. The steps in this vascular detection subroutine may include without limitation:

1. Only accepting clusters having between a certain number of members (e.g., between 3 and 500 members). Depending on the number of members, there may be a look-up table to specify (1) the order of the polynomial, (2) the threshold tolerance in the fit, and (3) the number of points that can be dropped. This may allow a higher-order fit and/or slightly larger tolerances for clusters with more members. In an aspect, only first order (linear) and second order polynomials are used, and the tolerance allowed varies from a range of values, e.g., 0.01 to 0.036. These tolerances may correspond to a normalized chi-squared of the fit (i.e., normalized to the length of the polynomial curve).

2. Next, the cluster may be rotated into a frame where the x-axis is aligned with the principal axis of the cluster computed above. A polynomial least-squares regression may be performed, and the chi-squared fit parameter can be computed and normalized by the length of the curve. If the fit is within tolerance, the cluster may be identified as vascular (type-1), otherwise the specified number of outlier points may be dropped, and the fit may be recomputed to see if the method 300 can find one within the tolerance specification.

3. For large vascular clusters, it may be difficult to fit with a second-order polynomial, especially if the cluster has multiple tree-like branches, or many outlier contours that are not well-aligned along the tubular structure. Thus, for large clusters the method 300 may attempt to split them into smaller subgroups, and then apply the polynomial fitting procedure to the subgroups. In an aspect, the method 300 has two different strategies for splitting and fitting, and the algorithm is set to employ one or both of these (i.e., apply the second if the first fails). If the routine finds any portion of the cluster that is well fit by 'q polynomial,' then the entire cluster may be classified as vascular.

4. Even with the above variations, it may be difficult to pick a tolerance for the fitting threshold that identifies all of the vascular clusters, while excluding ones that are potentially malignant. Thus, the method 300 may include a final check that applies to clusters that have a fitting tolerance somewhat above the threshold (and thus would not be identified as type-1), but where the principal axis aligns with a clear vascular cluster. Often a series of vascular clusters will form along the same vessel, or along a neighboring vessel. As a result, the principal axes of these two clusters may be well-aligned, they may be in the same proximity, and they often have a high aspect ratio (see cluster properties described above in step 336). Thus, by introducing a final check on these other factors, the method 300 may be able to identify and exclude additional vascular clusters.

Type-2: Large Calcifications and Fatty Necrosis

Another common type of benign clusters is associated with larger calcifications and fatty necrosis. These clusters may include larger members, with areas that may be significantly larger than micro-calcifications associated with malignancy. For clusters comprised entirely of larger calcifications, the 'Q score' described below may be relatively small. However, in other cases, there may be an overlap in the relevant range of areas with malignant clusters. Furthermore, the method 300 may find a number of smaller structures in the vicinity of the larger calcifications, which can then give rise to false-positives as described below.

In terms of geometric properties, these benign clusters may be characterized by relatively larger areas and by their fairly dense grouping. To this end, a cluster library may be created in which the geometric and contrast properties described above are extracted for interesting clusters for use and evaluation by the method 300. The cluster library may show that malignant clusters tend to be more dispersed (lower $P_f$) with a smaller range of areas, while the benign clusters are more densely packed (larger $P_f$) and/or larger areas. An approximate threshold curve to identify type-2 clusters may be provided as a line such as:

$$P_f = 0.85 - 0.6 < A_i > A_{max},\qquad \text{(Eq. 10)}$$

where $<A_i>$ is the average area of the calcifications within the cluster, $A_{max}$ is the area of the largest calcification in the cluster, and $P_f$ is the packing fraction (see description above). In a n aspect, this criteria is used to identify and exclude these benign clusters. While this may lead to some misclassifications, it may not greatly impact scoring metrics, since the malignant clusters are often correctly identified in other images/views, and for the rare times they are misclassified, this only occurs in one of the images/views. In another aspect, active contouring techniques are used to remedy misclassifications.

Type-3: Diffuse Round Calcifications

Another type of false-positive may be clusters that are characterized by diffuse, nearly circular calcifications. These are often fairly bright and have relatively good contrast, and thus many calcifications are often identified. The range of calcification sizes may be relatively similar to malignant micro-calcifications, but they tend to be spread over broader areas of the tissue (e.g., breast tissue), and also they may often appear on both sides in a similar manner. A technique for identifying these clusters uses the $C_{ratio}$ and $P_f$. Another technique may compare different sides of an image, e.g., comparing the left and right sides.

As shown in step 342, the method 300 may include quantifying clusters with a 'Q score.' The Q score as discussed herein may refer to a measurement, e.g., a number that quantifies the likelihood of malignancy for each cluster.

The Q score may include an analytic function of the geometric and contrast properties of the calcifications within each cluster, as well as their detailed spatial arrangements. The Q score may quantify aspects of the calcifications more quickly, accurately, and consistently than is possible for a human. In comparison to the black box approach of a neural net, the Q score enables a clear explanation in physical terms about how the method 300 is scoring any given cluster.

Some features built into the functional form for the Q score have already been discussed above in association with the grouping parameter $dQ_i$. It is well-established that clusters of micro-calcifications associated with cancer occur for a fairly limited range of spatial scales and separation distances. As the cancer develops from an early phase, the number of visible micro-calcifications will increase, along with the intensity and contrast of each visible calcification. To this end, the function may increase monotonically with these features, and allow sufficient flexibility to adjust free scaling parameters in order to optimize the overall performance. An example of this function is:

$$Q = \left(\frac{M_o}{M_o + M}\right) \sum_{i=1}^{M} \sum_{j=i+1}^{M} q_i q_j F(r_{min}, r_{max}, r_{ij}), \qquad \text{(Eq. 11)}$$

-continued $$= \left(\frac{M_o}{M_o + M}\right) \sum_{i=1}^{M} dQ_i,$$

where $M_0$ is a free parameter, M is the number of calcifications in the clusters, and all other symbols have been defined herein. The Q parameter may be roughly analogous to a potential energy or the like for the cluster (assuming a particular form for the pair-wise interactions), where the free scaling parameters have been adjusted to maximize the energy for malignant clusters. Aside from a normalization factor, the Q parameter defined in Eq. 11 may be a sum over the clustering parameter for each calcification (see Eq. 5). From this point of view, the approach for selecting calcifications may be connected with the overall strategy for scoring the significance of the final clusters.

To determine the free scaling parameters, a program performing a multi-dimensional optimization may be used in order to find values that maximize the area under the curve ("auc") for the receiver operating characteristic (ROC) curve. Example values for these parameters are as follows: $a_{min}=0.054$ mm$^2$, $a_{max}=0.42$ mm$^2$, $r_{min}=0.0$ mm, $r_{max}=2.69$ mm, $N_{max}=5$, $M_0=10$.

As shown in step 344, the method 300 may include saving results. For example, after completing the analysis for each image, the following results may be saved, which are provided by way of example and not of limitation:

1. List of clusters identified in the image, including the Q score and the cluster properties;

2. Outer contours for each of the calcifications within each cluster, along with the geometric and contrast properties for each of these shapes; and 3. Information to generate the ROC curves. This information may be extracted and saved along with the Q score for each cluster.

It will be understood that any values recited above with respect to the method 300 (or otherwise herein) are provided by way of example only, and are not meant to limit the embodiments described herein. These values may also or instead include predetermined (e.g., "best practice") values, e.g., discovered through a trial and error process. These values may be varied by a user or administrator, e.g., using a graphical user interface that includes fields for inputting the values.

FIG. 4 depicts a medical image of calcifications in a patient's tissue. The image 400 in the figure may represent an original medical image of a patient's tissue, e.g., a mammogram or the like. The image 400 may include calcifications 402, which may need to be identified for detecting whether cancer is present. In other words, the image 400 may be used in the devices, systems, and methods described herein for detecting and quantifying cancer in a patient's tissue shown therein.

FIG. 5 illustrates an example of a selection process for a malignant cluster of micro-calcifications. Specifically, the figure includes a first image 510 and a second image 520. The first image 510 may represent the contours 512 selected by any of the criteria outlined above. More specifically, these may be the contours 512 before they are grouped into nested hierarchies. The calcifications most noticeable to the human eye may have many nested contours 512, which are grouped together into nested structures as described above (these nested structures are shown, for example by the bubbled area 514 in the figure). These internal nested contours 512 may be used to evaluate gradients in the intensity across the structure (see δA and δI parameters defined in the equation above), and the parameter $dQ_i$ may be used to characterize the groupings (as explained above). The final calcifications 522 shown in the second image 520 may be selected according to the criteria described above with respect to step 330 of the method 300. Specifically, the second image 520 shows the outer boundaries of these final selected calcifications 522.

Figure 6:
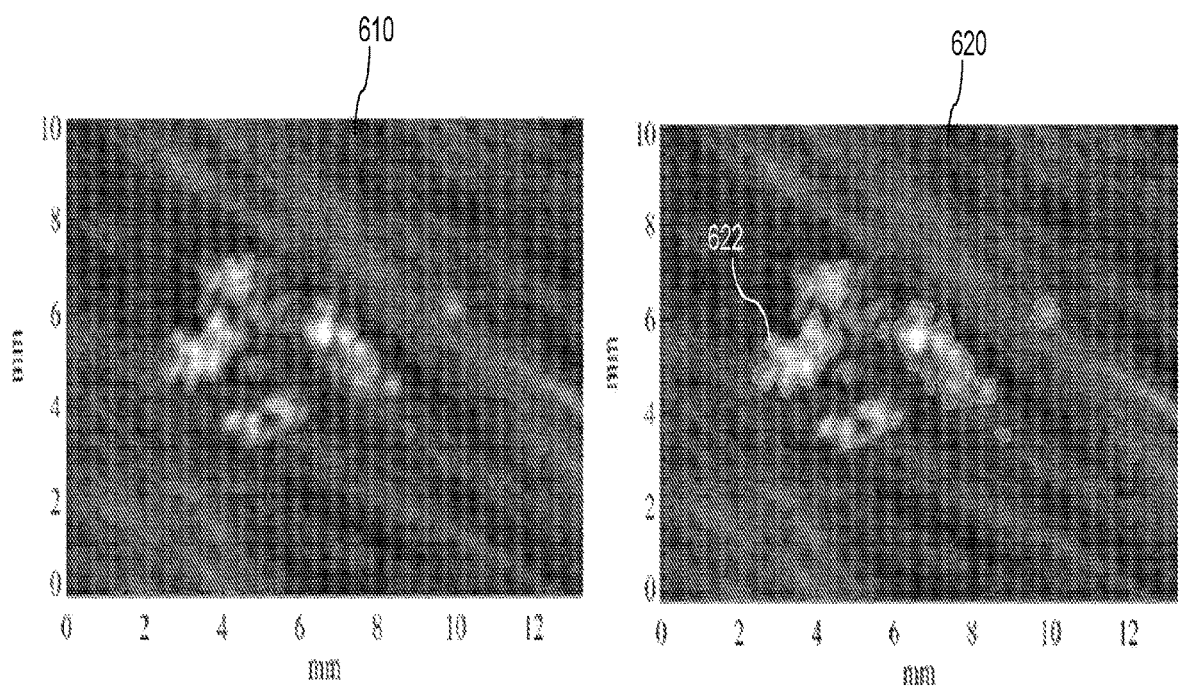
FIG. 6 illustrates an example of the identification of a cluster of calcifications.

FIG. 6 illustrates an example of the identification of a cluster of calcifications. For example, the figure shows the identification of type-2 clusters with fatty necrosis using techniques described herein. The figure includes a first image 610 and a second image 620. The first image 610 shows an original medical image of tissue without any overlaid contours. The second image 612 shows contours 622 identified by the techniques described herein, e.g., the method described with reference to FIG. 3, which may utilize one or more algorithms.

Figure 7:
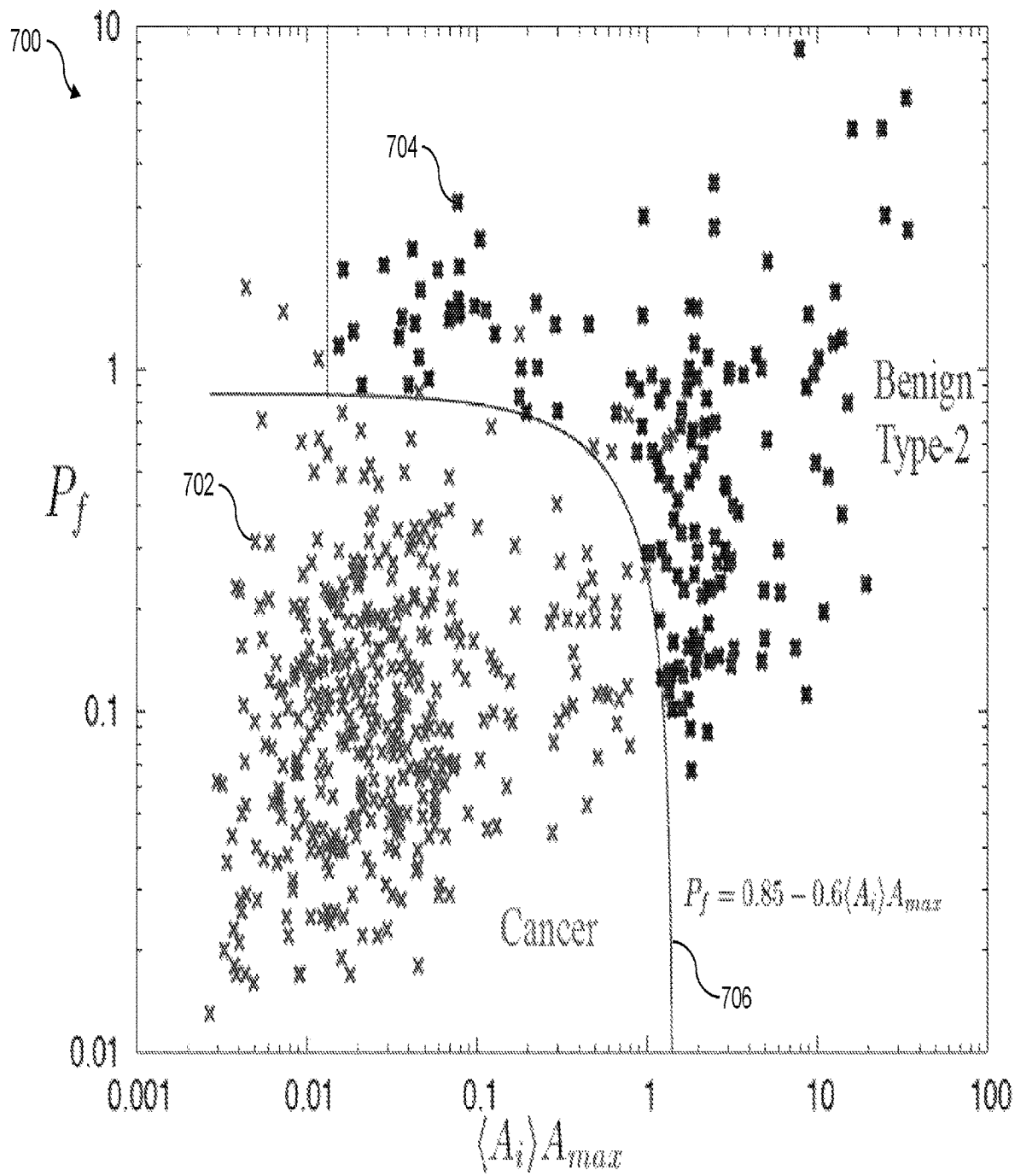
FIG. 7 is a graph showing an example of a packing fraction as a function of $<A_i>A_{max}$ for exemplary clusters.

FIG. 7 is a graph showing an example of a packing fraction as a function of $<A_i>A_{max}$ for exemplary clusters. Specifically, in the graph 700, the x-axis is the $<A_i>A_{max}$, where $<A_i>$ is the average area of the calcifications within the cluster and $A_{max}$ is the area of the largest calcification in the cluster. In the graph 700, the y-axis is the $P_f$, i.e., the packing fraction (see discussion above).

In the graph 700, the lighter lineweight points 702 correspond to malignant clusters, while the heavier lineweight points 704 correspond to various type-2 clusters. In this specific graph 700, only clusters with less than 30 calcifications are included for clarity and by way of example, but clusters with more calcifications may also or instead be used. An approximate boundary separating the benign from malignant clusters is given by the line 706.

In general, the figure may represent the derivation of criteria for identifying type-2 clusters that are used in the techniques described herein, where each point in the graph 700 corresponds to a single cluster in an exemplary study, which was used to refine the techniques described herein. The results show that malignant clusters tend to be more dispersed (lower $P_f$) with a smaller range of areas, while the benign clusters are more densely packed (larger $P_f$) and/or larger areas. An approximate threshold curve to identify type-2 clusters may be provided by the line 706, which may take the form:

$$P_f = 0.85 - 0.6 <A_i>A_{max}$$

In an implementation, this is the criteria used to identify and exclude benign clusters. As shown in the graph 700, the malignant points to the right of the line 706 may be misclassified as benign type-2. While this may be undesirable, it also may not impact the scoring metrics described herein, as discussed above. As further shown, it appears that the outer boundaries corresponding to the calcifications may be too large and/or encompasses multiple smaller calcifications. This may cause the measured areas to be larger than they should be, and thus may move the cluster into the benign region of the parameters space in the figure. This can be improved upon by utilizing advancements in the contouring techniques, e.g., active contouring techniques.

As discussed herein, an implementation may include a method for determining a cancer score. Determining a cancer score may be accomplished through the user of a cancer score engine (and its components) or the like as described herein. In the method, an event of interest may be defined. An event of interest may be any object of interest to be identified from data. Examples of events may be cancerous lesions, masses, physiological anomalies, and the like.

The method may gather variables for the events of interest, such as x1, x2 . . . xn. The variables may be a minimum number of variables that allow the event to be predicted and a score to be generated, e.g., a cancer score. The variables may be gathered by identifying a number of variables and then discarding variables that are not predictive and/or show the wrong behavior for the event of interest. In one implementation, the event of interest may be breast cancer and the variables may include closed intensity contours of calcifications in mammogram images, gradients of the calcifications, one or more characteristics about each calcification, such as perimeter, contrast and/or a number of neighbors, a texture and shape of each calcification and/or a hierarchical structure of the calcifications in a cluster, such as how tightly the calcifications are nested, if there are nested levels of calcifications and the like. The variables for mammogram images may also or instead include other variables. This method may also include a clustering of individual calcifications with their neighbors and then grouping into prototype clusters which may be ordered based on a number of neighbors. In the breast cancer example, the values of these variables may be determined by the computer analysis of the mammogram images.

The method may calculate a Q0 based on the values of the variables, where Q0 is an analytical function of the variables so that Q0=F(x1, x2, . . . , xn). Thus, in the breast cancer implementation, the method may calculate Q0 for each cluster of calcifications in which Q0 is a function of the variables calculated over each cluster. For example, Q0 may include use of any of the functions described herein.

The method may calculate a Q1, where Q1 is equal to (Q0)×(a penalty function). The penalty function may selected be such that Q1 incorporates a classification scheme. In the breast cancer implementation, the penalty function may discard calcifications that are spaced too far apart and thus are unlikely to be suspicious cells. The method may then normalize Q1 to generate a cancer score. During the normalization, the parameters of Q0 and Q1 may be optimized to maximize the area under a well-known (ROC) or free receiver operating characteristic (FROC) curve. By way of example, the FROC curves are described in Bornefalk et al., "On the Comparison of FROC curves in Mammography CAD Systems", Med. Phys. 32, pp. 412-17 (2005), which is hereby incorporated by reference in its entirety. Thus, based on the above curves, the cancer score may have thresholds and classify the clusters of calcifications into Type-1, Type-2 and Type-3, where Type-1 identifies a linear or curvilinear cluster (benign lesion), Type-2 identifies a cluster that has one or more calcification members that are exceptionally large and/or bright in the mammogram image, and Type-3 identifies a cluster that is likely malignant. The method may display the cancer score in some form. For example, as shown in figures included herein of medical images, a cluster of calcifications may be classified as cancerous thereby warranting a biopsy.

Figure 8:
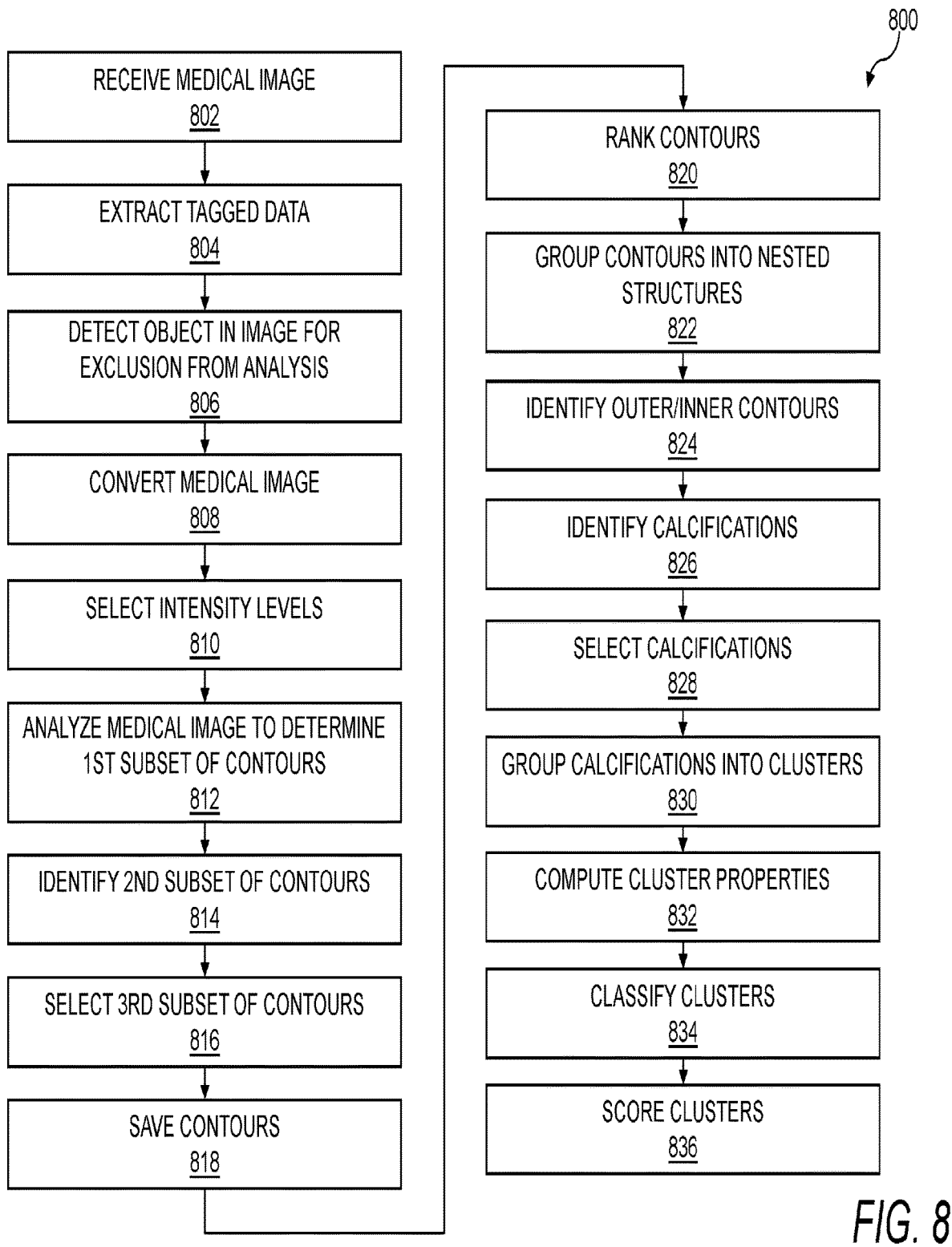
FIG. 8 is a flow chart of a method for cancer detection and quantification.

FIG. 8 is a flow chart of a method for cancer detection and quantification.

As shown in step 802, the method 800 may include receiving a medical image, e.g., through a communications interface of a computing device over a data network. The medical image may include one or more of an x-ray image, a computerized tomography (CT) scan, a magnetic resonance (MRI) image, and an ultrasound image. One or more of the steps of the method 800 may be completed by a processor or the like, e.g., a processor executing code embodied in a non-transitory computer readable medium.

The processor may be included as part of a computing device upon which the medical image is received.

As shown in step 804, the method 800 may include extracting tagged data from the medical image, e.g., where the medical image is included in a computer file. The tagged data may include one or more of a side, a pixel spacing, an orientation, a protocol, and a date. The tagged data may be included in a Digital Imaging and Communications in Medicine (DICOM) header. The tagged data may include metadata, data shown on an image (e.g., stamped on the image), or the like.

As shown in step 806, the method 800 may include detecting an object in the image for exclusion from further analysis. The object may be an external object. The object may be detected through the object having at least one of: an area greater than a predetermined area, an intensity greater than a predetermined intensity, and a circle ratio greater than a predetermined circle ratio.

As shown in step 808, the method 800 may include converting the medical image to a 4-byte real array of intensities for contouring.

As shown in step 810, the method 800 may include selecting intensity levels for determining contours in the medical image.

As shown in step 812, the method 800 may include analyzing the medical image to determine a first subset of contours in the medical image satisfying one or more criterion. The one or more criterion may include that each contour in the first subset of contours is (i) closed and (ii) includes a contour value larger than a surrounding area external to the contour. In an aspect, contours not satisfying the one or more criterion are discarded.

As shown in step 814, the method 800 may include analyzing one or more geometric attributes and one or more contrast attributes of contours included in the first subset of contours to identify a second subset of contours based upon contours satisfying one or more predetermined geometric and contrast attributes. The one or more geometric attributes of contours may include at least one of: a centroid, an area, a perimeter, a circle ratio, and an interior flag. The one or more contrast attributes of contours may include at least one of: an intensity, an inward contrast, an outward contrast, and a gradient scale.

As shown in step 816, the method 800 may include selecting a third subset of contours from the second subset of contours that corresponds to potential calcifications. The third subset of contours may be selected based on contours within the second subset satisfying first calcification criteria. Selecting the third subset of contours may include excluding contours located within a predetermined distance from at least one of an edge of the medical image and an edge of tissue.

The first calcification criteria may include contours having a predetermined area and a predetermined gradient scale. The predetermined area may be between about 0.003 $mm^2$ and about 800 $mm^2$, and the predetermined gradient scale may be less than about 1.3 mm. The first calcification criteria may also or instead include contours having a predetermined intensity, a predetermined circle ratio, a predetermined inward contrast, and a predetermined outward contrast. The predetermined intensity may be greater than about 0.67 times a maximum intensity, the predetermined circle ratio may be greater than about 0.65, the predetermined inward contrast may be greater than about 1.06, and the predetermined outward contrast may be greater than about 1.22. The first calcification criteria may also or instead include contours having a predetermined area, a predetermined circle ratio, and at least one of a predetermined inward contrast and a predetermined gradient scale. The predetermined area may be less than about 0.30 $mm^2$, the predetermined circle ratio may be greater than about 0.65, the predetermined inward contrast may be greater than about 1.04, and the predetermined gradient scale may be greater than about 0.3 mm. The first calcification criteria may also or instead include contours having a predetermined area, a predetermined circle ratio, and a predetermined intensity.

As shown in step 818, the method 800 may include saving the third subset of contours, e.g., in a memory of the computing device.

As shown in step 820, the method 800 may include ranking contours included in the third subset of contours based on a selection metric. The selection metric may account for a combination of contrast and intensity.

As shown in step 822, the method 800 may include grouping contours included in the third subset of contours into nested structures.

As shown in step 824, the method 800 may include identifying outer contours in each nested structure representing a contour shape and inner contours in each nested structure providing data on internal gradients.

As shown in step 826, the method 800 may include identifying calcifications for each nested structure based on at least one of: a contour derivative and a grouping parameter computed for each nested structure. The contour derivative may measure how rapidly intensity varies across a nested structure.

As shown in step 828, the method 800 may include selecting calcifications from the nested structures satisfying second calcification criteria. The second calcification criteria may include a threshold on a contour derivate and a threshold on a grouping parameter.

As shown in step 830, the method 800 may include grouping the selected calcifications into clusters, e.g., based on one or more of neighboring calcifications and a spatial cluster scale.

As shown in step 832, the method 800 may include computing cluster properties with the processor. The cluster properties may include one or more of a cluster centroid, a cluster half-length, a cluster half-width, an aspect ratio, a principal axis, and a packing fraction.

As shown in step 834, the method 800 may include classifying the clusters as benign or possible cancer by performing one or more of: a regression analysis on calcifications within the clusters, edge detection, a density analysis of the clusters, and a circularity analysis of the clusters.

As shown in step 836, the method 800 may include scoring the clusters using an analytic function of geometric and contrast properties of the calcifications within each cluster, and spatial arrangements of the calcifications within each cluster.

In an aspect, a computer program product may include non-transitory computer executable code embodied in a non-transitory computer readable medium that, when executing on one or more computing devices, performs the steps of: receiving a medical image through a communications interface of a computing device over a data network; analyzing the medical image to determine a first subset of contours in the medical image satisfying one or more criterion; analyzing one or more geometric attributes and one or more contrast attributes of contours included in the first subset of contours to identify a second subset of contours based upon contours satisfying one or more predetermined geometric and contrast attributes; selecting a third subset of contours from the second subset of contours that corresponds to potential calcifications, the third subset selected based on contours within the second subset satisfying first calcification criteria; ranking contours included in the third subset of contours based on a selection metric, the selection metric accounting for a combination of contrast and intensity; grouping the contours included in the third subset of contours into nested structures; selecting calcifications from the nested structures satisfying second calcification criteria; grouping the selected calcifications into clusters based on one or more of neighboring calcifications and a spatial cluster scale; classifying the clusters as benign or possible cancer by performing one or more of: a regression analysis on calcifications within the clusters, edge detection, a density analysis of the clusters, and a circularity analysis of the clusters; and scoring the clusters using an analytic function of: geometric and contrast properties of the calcifications within each cluster, and spatial arrangements of the calcifications within each cluster.

In an aspect, a system may include a computing device including a network interface for communications over a data network, and a cancer score engine having a processor and a memory. The cancer score engine may include a network interface for communications over the data network. The cancer score engine may be configured to receive a medical image from the computing device. The memory may be configured to store the medical image. The processor may be configured to analyze the medical image, generate a cancer score for the medical image, and transmit the cancer score to the computing device for display on a user interface thereof. Analysis of the medical image may include: determining a first subset of contours in the medical image satisfying one or more criterion; analyzing one or more geometric attributes and one or more contrast attributes of contours included in the first subset of contours to identify a second subset of contours based upon contours satisfying one or more predetermined geometric and contrast attributes; selecting a third subset of contours from the second subset of contours that corresponds to potential calcifications, the third subset selected based on contours within the second subset satisfying first calcification criteria; ranking contours included in the third subset of contours based on a selection metric, the selection metric accounting for a combination of contrast and intensity; grouping the contours included in the third subset of contours into nested structures; selecting calcifications from the nested structures satisfying second calcification criteria; grouping the selected calcifications into clusters based on one or more of neighboring calcifications and a spatial cluster scale; classifying the clusters as benign or possible cancer by performing one or more of: a regression analysis on calcifications within the clusters, edge detection, a density analysis of the clusters, and a circularity analysis of the clusters; and scoring the clusters using an analytic function to generate the cancer score.

In an aspect, a computer-implemented method may include: receiving one or more pieces of medical information for processing and analysis on a computing device, the one or more pieces of medical information including a medical image of tissue; analyzing, with a processor of the computing device, a region of the medical image to determine a presence of one or more contours in the region; extracting, with the processor, one or more properties of the one or more contours; inputting, with the processor, the one or more properties into a first algorithm to determine an indication of cancer for the region; inputting, with the processor, the indication of cancer into a second algorithm to generate a cancer score for the region; and generating the cancer score for the region.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings The systems and methods disclosed herein may be implemented via one or more components, systems, servers, appliances, other subcomponents, or distributed between such elements. When implemented as a system, such systems may include an/or involve, inter alia, components such as software modules, general-purpose CPU, RAM, etc., found in general-purpose computers. In implementations where the innovations reside on a server, such a server may include or involve components such as CPU, RAM, etc., such as those found in general-purpose computers.

Additionally, the systems and methods herein may be achieved via implementations with disparate or entirely different software, hardware and/or firmware components, beyond that set forth above. With regard to such other components (e.g., software, processing components, etc.) and/or computer-readable media associated with or embodying the present implementations, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the systems and methods may be achieved via or performed by logic and/or logic instructions including program modules, executed in association with such components or circuitry, for example. In general, program modules may include routines, programs, objects, components, data structures, etc., that perform particular tasks or implement particular instructions herein. The embodiments may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, where media of any type herein does not include transitory media. Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the implementations described herein or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the implementations herein, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Additionally, the words "herein," "hereunder," "above," "below," and words of similar import refer to this application as a whole and not to any particular portions of this application.

Moreover, the above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed:

1. A computer-implemented method comprising:
receiving one or more pieces of medical information for processing and analysis on a computing device, the one or more pieces of medical information including a medical image of tissue;
analyzing the medical image for one or more anomalies, wherein the analyzing comprises determining contours in the medical images based on geometric and contrast attributes in the medical images, wherein the contours correspond to potential calcifications, a subset of the contours satisfy calcification criteria and the one or more anomalies comprises one or more groups of contours in the subset of the contours arranged in spatial clusters based on a number of neighboring calcifications and a spatial cluster scale;
extracting one or more properties of the one or more anomalies, wherein the one or more properties of the one or more anomalies comprises one or more moments of a distribution of calcification within a given spatial cluster in the spatial clusters;
inputting the one or more properties into one or more algorithms to determine a cancer score based on the one or more anomalies; and
generating the cancer score.

2. The computer-implemented method of claim 1, wherein the medical image includes one or more of an x-ray image, a computerized tomography (CT) scan, a magnetic resonance (MM) image, and an ultrasound image.

3. The computer-implemented method of claim 1, wherein the cancer score is generated by a cancer score engine having a processor.

4. The computer-implemented method of claim 3, wherein the processor analyzes the medical image, generates the cancer score, and transmits the cancer score to the computing device for display on a user interface.

5. The computer-implemented method of claim 3, wherein the cancer score engine generates one or more cancer scores about one or more regions in a piece of tissue.

6. The computer-implemented method of claim 3, wherein the cancer score engine comprises one of a microcontroller, programmable logic device, and an application specific integrated circuit.

7. The computer-implemented method of claim 3, wherein the cancer score engine has a memory.

8. The computer-implemented method of claim 7, where the memory is configured to store the medical image.

9. The computer-implemented method of claim 1, wherein the calcification criteria comprises two or more of predefined or predetermined: area, gradient scale, circle ratio and intensity.

10. The computer-implemented method of claim 1, wherein the cancer score indicates a likelihood of having cancer.

11. The computer-implemented method of claim 10, wherein the cancer is selected from the group consisting of breast, brain, lung, liver, prostate, bone, cervical, colon, leukemia, Hodgkin disease, kidney, lymphoma, oral, skin, stomach, testicular, and thyroid.

12. The computer-implemented method of claim 1, wherein the cancer score is indicated by a numerical score.

13. The computer-implemented method of claim 12, wherein the numerical score closer to zero indicates low likelihood of cancer, and the numerical score further from zero indicates higher likelihood of cancer.

14. The computer-implemented method of claim 1, wherein the cancer score is indicated by discrete categories.

15. The computer-implemented method of claim 1, wherein the cancer score is compared to an assessment by a medical image reader to determine false positives and false negatives.

16. The computer-implemented method of claim 1, wherein the cancer score is changeable based on one of growth and shrinkage of cancer cells/tumors.

17. The computer-implemented method of claim 1, wherein the medical image is of one of human tissue and non-human animal tissue.

18. The computer-implemented method of claim 1, wherein the cancer score identifies an area of interest.

19. The computer-implemented method of claim 18, wherein the area of interest is selected from the group consisting of calcifications, lesions, masses, and tumors.

20. The computer-implemented method of claim 19, wherein the area of interest is identifiable by variable values selected from the group consisting of intensity, hierarchical structure, and gradient.

\* \* \* \* \*